(12) United States Patent
Cangialosi et al.

(10) Patent No.: US 12,227,624 B2
(45) Date of Patent: Feb. 18, 2025

(54) MOLECULAR DNA STRAND-DISPLACEMENT CONTROLLERS FOR DIRECTING MATERIAL EXPANSION

(71) Applicant: THE JOHNS HOPKINS UNIVERSITY, Baltimore, MD (US)

(72) Inventors: Angelo Cangialosi, Baltimore, MD (US); ChangKyu Yoon, Timonium, MD (US); Joshua Fern, Baltimore, MD (US); Thao D. Nguyen, Baltimore, MD (US); David H. Gracias, Baltimore, MD (US); Rebecca Schulman, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1219 days.

(21) Appl. No.: 16/964,467

(22) PCT Filed: Jan. 22, 2019

(86) PCT No.: PCT/US2019/014439
§ 371 (c)(1),
(2) Date: Jul. 23, 2020

(87) PCT Pub. No.: WO2019/156801
PCT Pub. Date: Aug. 15, 2019

(65) Prior Publication Data
US 2021/0047478 A1 Feb. 18, 2021

Related U.S. Application Data

(60) Provisional application No. 62/620,669, filed on Jan. 23, 2018.

(51) Int. Cl.
*C12Q 1/6806* (2018.01)
*C08J 3/075* (2006.01)

(52) U.S. Cl.
CPC ............ *C08J 3/075* (2013.01); *C12Q 1/6806* (2013.01)

(58) Field of Classification Search
None
See application file for complete search history.

(56) References Cited

U.S. PATENT DOCUMENTS

2004/0059102 A1* 3/2004 Mills, Jr. ............. C12Q 1/6876
536/23.1

OTHER PUBLICATIONS

Lilienthal et al. Programmed DNAzyme-Triggered Dissolution of DNA-Based Hydrogels: Means for Controlled Release of Biocatalysts and for the Activation of Enzyme Cascades. ACS Appl. Mater. Interfaces, 2015, 7, 8923-8931. (Year: 2015).*

(Continued)

*Primary Examiner* — Stephen E Rieth
(74) *Attorney, Agent, or Firm* — Casimir Jones, S.C.; Kelly A. Barton

(57) ABSTRACT

The present disclosure provides compositions and methods including modular material controllers that combine amplification with logic, translation of input signals, and response tuning to directly and precisely program dramatic material size changes. In particular, the present disclosure provides locked gels having a polymer with a nucleic acid cross link and a nucleic acid lock in a locked conformation preventing the locked gel from reacting with other nucleic acid sequences and methods of unlocking the locked gels by adding a nucleic acid key to the locked gel or by changing an inactive nucleic acid key into an active nucleic acid key with a trigger.

6 Claims, 23 Drawing Sheets
Specification includes a Sequence Listing.

(56) References Cited

OTHER PUBLICATIONS

Gawal et al. Logic swelling response of DNA-polymer hybrid hydrogel. Soft Matter, 2011, 7, 4615-4618. (Year: 2011).*
Lu et al. Multitriggered Shape-Memory Acrylamide-DNA Hydrogels. J. Am. Chem. Soc. 2015, 137, 15723-15731. (Year: 2015).*
Wahl et al., Molecular Hybridization of Immobilized Nucleic Acids: Theoretical Concepts and Practical Considerations (1987) Methods Enzymol. 152:399.
Kimmel., Identification and characterization of specific clones: Strategy for confirming the validity of presumptive clones., (1987) Methods Enzymol. 152:507.
Benton et al., Screening lambdagt recombinant clones by hybridization to single plaques in situ., Science 1977, 196:180.
Grunstein et al., Colony hybridization: a method for the isolation of cloned DNAs that contain a specific gene., Proc. Natl. Acad. Sci. USA 72:3961, 1975.
Stoney., The Tension of Metallic Films Deposited by Electrolysis. Proc. R. Soc. London A Math. Phys. Eng. Sci. 82, 172-175 (1909).
Ogden., Large Deformation Isotropic Elasticity: On the Correlation of Theory and Experiment for Compressible Rubberlike Solids. Proc. R. Soc. London A Math. Phys. Eng. Sci. 328, 567-583 (1972).
Breger et al., Self-folding thermo-magnetically responsive soft microgrippers. ACS Appl. Mater. Interfaces. 7, 3398-3405 (2015).
Zadeh et al. Nupack: analysis and design of nucleic acid systems. J. Comput. Chem. 32, 170-3 (2011).
Seelig et al., Enzyme-free nucleic acid logic circuits. Science 314, 1585-8 (2006).
Qian et al., Scaling up digital circuit computation with DNA strand displacement cascades. Science 332, 1196-201 (2011).
Ionov., Biomimetic hydrogel-based actuating systems. Adv. Funct. Mater. 23, 4555-4570 (2013).
Jeon et al., Shape-Morphing Materials from Stimuli-Responsive Hydrogel Hybrids. Acc. Chem. Res. 50, 161-169 (2017).
Gracias., Stimuli responsive self-folding using thin polymer films. Curr. Opin. Chem. Eng. 2, 112-119 (2013).
Liu et al., Self-folding of polymer sheets using local light absorption. Soft Matter. 8, 1764 (2012).
Zarzar et al., Stimuli-responsive chemomechanical actuation: A hybrid materials approach. Acc. Chem. Res. 47, 530-539 (2014).
Rus et al., Design, fabrication and control of soft robots. Nature. 521, 467-475 (2015).
Lievski et al., Soft robotics for chemists. Angew. Chemie—Int. Ed. 50, 1890-1895 (2011).
Hawkes et al., Programmable matter by folding. Proc. Natl. Acad. Sci. 107, 12441-12445 (2010).
Postma et al., Preprogramming Complex Hydrogel Responses using Enzymatic Reaction Networks. Angew. Chemie Int. Ed., 1-6 (2017).
Ikeda et al., Installing logic-gate responses to a variety of biological substances in supramolecular hydrogelenzyme hybrids. Nat. Chem. 6, 511-8 (2014).
Zhang et al., Dynamic DNA nanotechnology using strand-displacement reactions. Nat. Chem. 3, 103-113 (2011).
Yan et al., A robust DNA mechanical device controlled by hybridization topology. Nature. 415, 62-65 (2002).
Shim et al., Shape changing thin films powered by DNA hybridization. Nat. Nanotechnol., 1-8 (2016).
Kim et al., Transmutable nanoparticles with reconfigurable surface ligands. Science 351 (2016).
Zhang et al., Selective transformations between nanoparticle superlattices via the reprogramming of DNA-mediated Interactions. Nat. Mater. 14, 840-847 (2015).
Nagahara et al., Hydrogel formation via hybridization of oligonucleotides derivatized in water-soluble vinyl polymers. Polym. Gels Networks. 4, 111-127 (1996).
Liedl et al., Controlled trapping and release of quantum dots in a DNA-switchable hydrogel. Small. 3, 1688-1693 (2007).
Wang et al., Bioresponsive DNA Hydrogels: Beyond the Conventional Stimuli Responsiveness., Acc. Chem. Res., in press, 2017, 50(4):733.
Hu et al., Reversible Modulation of DNA-Based Hydrogel Shapes by Internal Stress Interactions. J. Am. Chem. Soc. 138, 16112-16119 (2016).
Lin et al., Inducing Reversible Stiffness Changes in DNAcrosslinked Gels. J. Mater. Res. 20, 1456-1464 (2005).
Zhang et al., Applicability range of Stoney's formula and modified formulas for a film/substrate bilayer. J. Appl. Phys. 99, 53513 (2006).
Venkataraman et al., An autonomous polymerization motor powered by DNA hybridization. Nat. Nanotechnol. 2, 490-494 (2007).
Yoon et al., Functional stimuli responsive hydrogel devices by self-folding. Smart Mater. Struct. 23, 94008 (2014).
Flory et al., Statistical Mechanics of Cross-Linked Polymer Networks I. Rubberlike Elasticity. J. Chem. Phys. 11, 512-520 (1943).
Freund et al., Extensions of the Stoney formula for substrate curvature to configurations with thin substrates or large deformations. Appl. Phys. Lett. 74, 1987-1989 (1999).
Chester et al., A coupled theory of fluid permeation and large deformations for elastomeric materials. J. Mech. Phys. Solids. 58, 1879-1906 (2010).
Hong et al., A theory of coupled diffusion and large deformation in polymeric gels. J. Mech. Phys. Solids. 56, 1779-1793 (2008).
Schulman et al., Robust self-replication of combinatorial information via crystal growth and scission. Proc. Natl. Acad. Sci. 109, 6405-6410 (2012).
Jamal et al., Bio-origami hydrogel scaffolds composed of photocrosslinked PEG bilayers. Adv. Healthc. Mater. 2, 1142-1150 (2013).
Linder et al., Water-soluble sacrificial layers for surface micromachining. Small. 1, 730-736 (2005).
Yurke et al., Mechanical Properties of a Reversible, DNA-Crosslinked Polyacrylamide Hydrogel. J. Biomech. Eng. 126, 104 (2004).
Tse et al., Preparation of hydrogel substrates with tunable mechanical properties. Curr. Protoc. Cell Biol., 1-16 (2010).
Kang, H., et al., "Photoresponsive DNA-Cross-Linked Hydrogels for Controllable Release and Cancer Therapy" Langmuir (2011) vol. 27, No. 1, pp. 399-408.
Yin, B., et al., "Colorimetric logic gates based on aptamer-crosslinked hydrogels" Chem. Commun., 2012, 48, 1248-1250.
Cangialosi, A., et al., "DNA sequence-directed shape change of photopatterned hydrogels via high-degree swelling" Science 357, 1126-1130 (2017).
Kahn, J., "Stimuli-Responsive DNA-Based Hydrogels: From Basic Principles to Applications" Acc. Chem. Res. 2017, 50, 680-690.
Fern, J., et al., "DNA Strand-Displacement Timer Circuits" ACS Synth. Biol. 2017, 6, 190-193.
Fern, J., et al., "Design and Characterization of DNA Strand-Displacement Circuits in Serum-Supplemented Cell Medium" ACS Synth. Biol. 2017, 6, 1774-1783.
Kang et al., Photoresponsive DNA-Cross-Linked Hydrogels for Controllable Release and Cancer Therapy, Langmuir 2011, 27(1): 399-408.
Zhou et al., Aptamer-based biosensors for biomedical diagnostics, Analyst 2014, 139: 2627-2640.

* cited by examiner

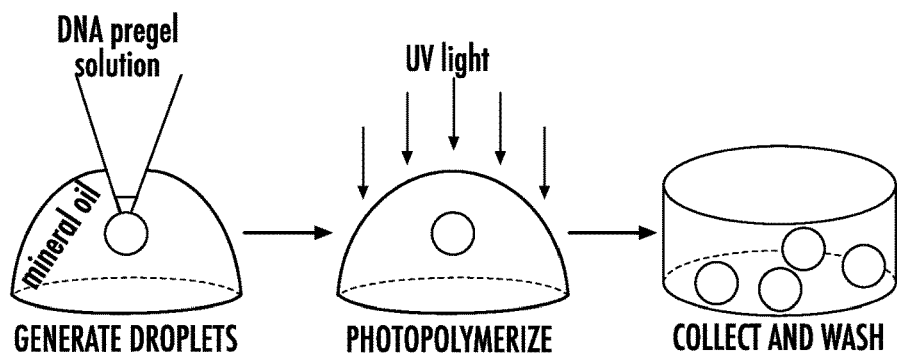
FIG. 2A
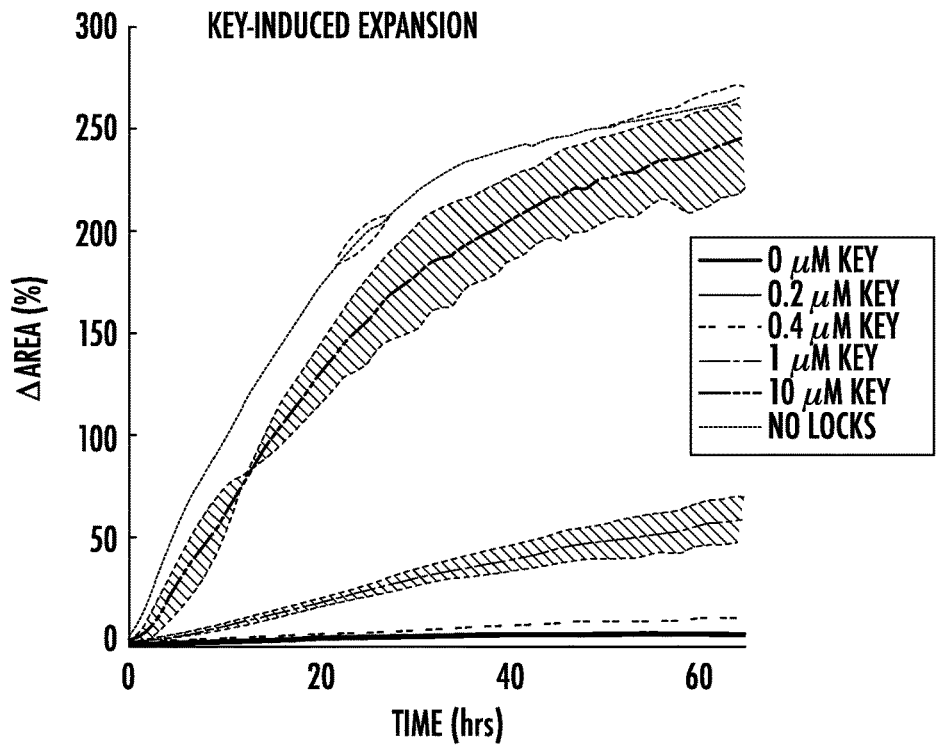
FIG. 2B
FIG. 2C

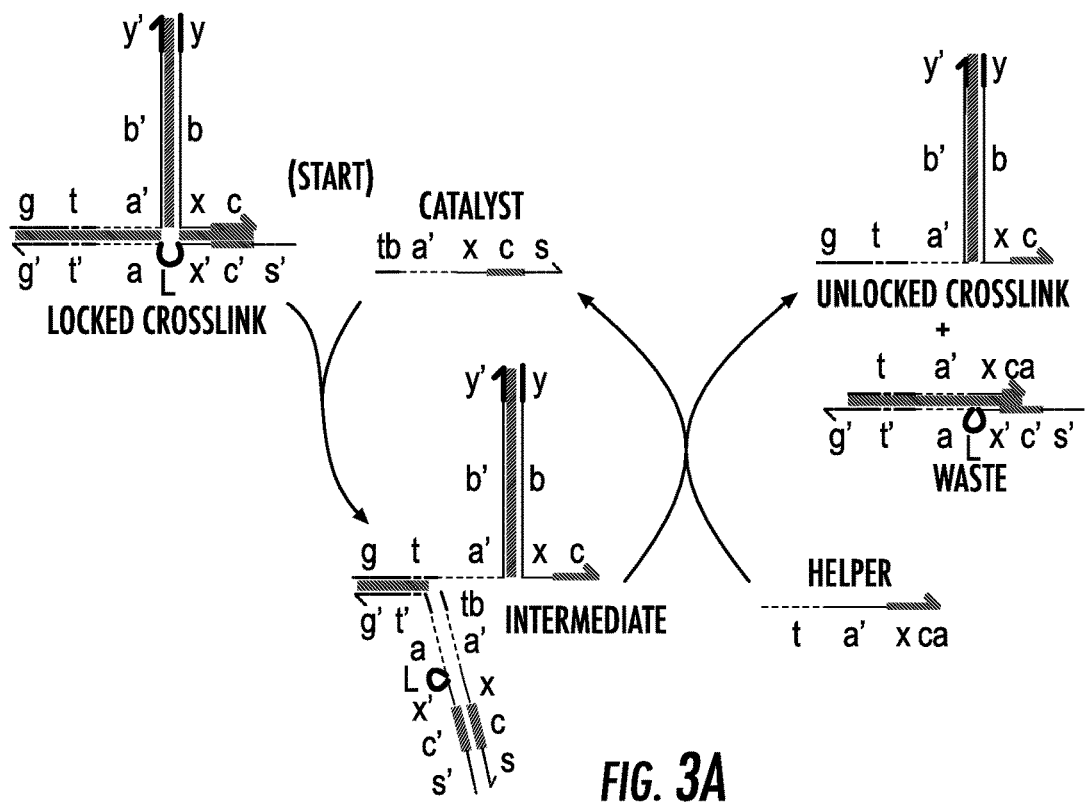
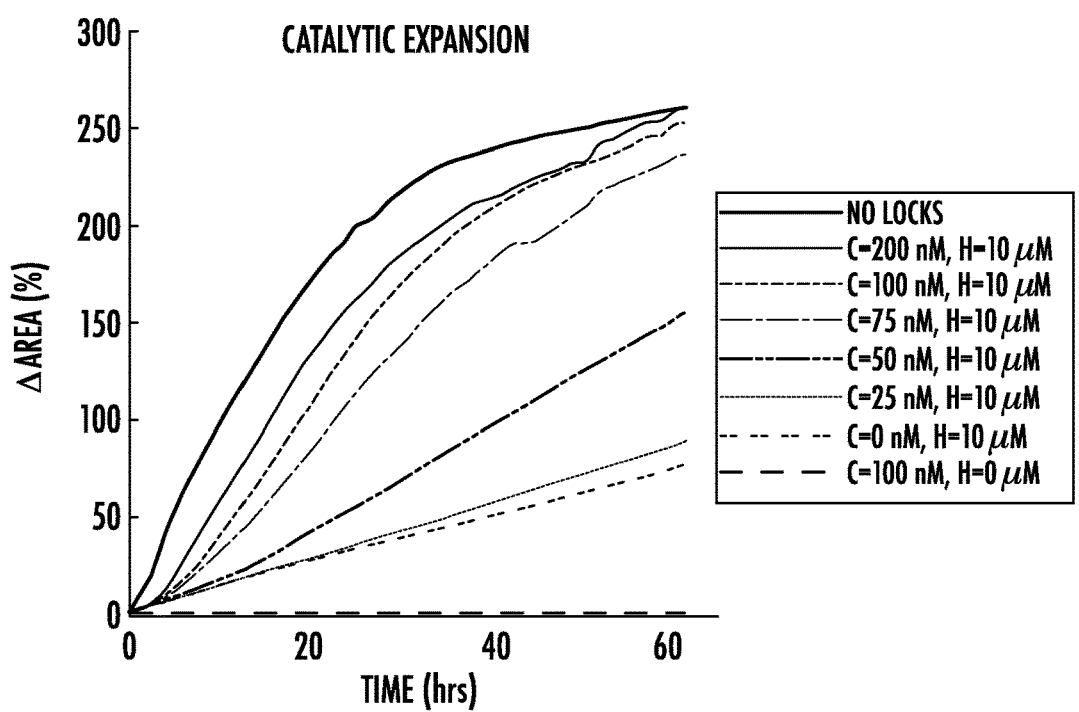
FIG. 3A
FIG. 3B

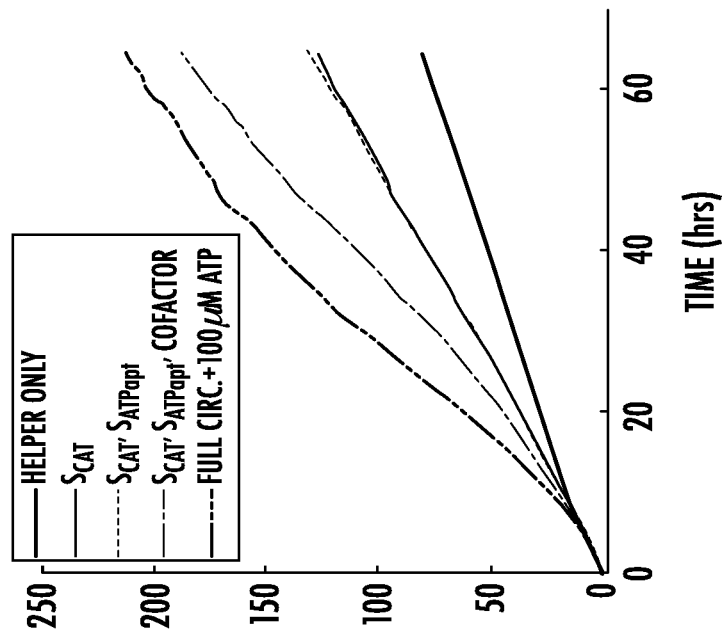
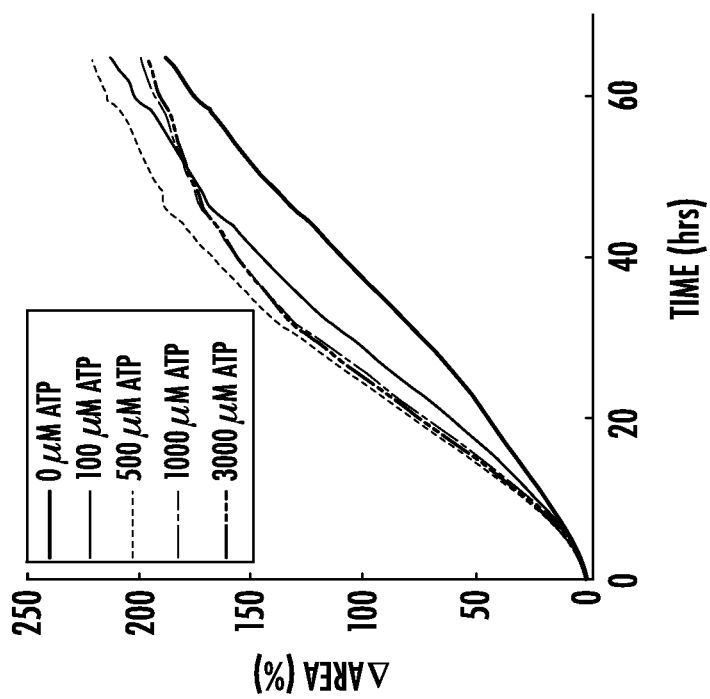
FIG. 19A
FIG. 19B

| | | |
|---|---|---|
| INPUT F$_{IN}$ | Ma cb s 7ac w mb r | GTTAGATGGAGATGTTGTGAGGAATGATTAAGGC |
| INPUT G$_{IN}$ | r' N q' | ATTCCGATTTCTAGTCCCTTGTGTAT |
| LOGIC GATE | Ma cb s 7 w mb r N q<br>Ma' cb' s' 7ac' w' mb' r' q' N' | GTTAGATGGAGATGTTGTGAGGAATGATTAAGGCTAAAGATCAGGGAACACCATA<br>CAATCTACCTCTACAACACTCCTTACTAATTCCGATTTCCTTAGTCCCTTG |
| E$_{OUT}$ | ma cbs 7 w mb<br>s' 7' | GTTAGATGGAGATGTAATTGATATGTGAGGAATGAT |
| CATALYST SOURCE | tb a' x c s 7<br>s' 7' w' | GTTAAGTTTGGGGTGAGATGTAATTGATATGT<br>CTCTACATTAACTATACACACTCCA |

FIG. 20

SEQUENCE LISTING

```
<160> NUMBER OF SEQ ID NOS: 37

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taagttcgct gtggcacctg cacg                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caacgtgcag gtgccacagc gtgg                                              24

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttgagtattg ttaagttcgc tgtggcacct gcacgttg                               38

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caacgtgcag gtgccacagc gtggggtgtt t                                      31

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggttaagtt cgctgtggca cctgcacgtt g                                      31

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caacgtgcag gtgccacagc gtgggg                                            26
```

```
<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttgttatgta tctgtctgcc taccactccg ttgcgaat                              38

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
attcgcaacg gagtggtagg ctttgaattt t                                     31

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atctcacccc ataacttaac aatactc                                          27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gagtattgtt aagttatggg gtgagat                                          27

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtattgttaa gtttgggg                                                    18

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gttaagtttg gggtgagat                                                   19
```

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccacgctgtg gcacctgcac gcacccacgt gcaggtgcca cagcgaactt a         51

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgggtgcgtg caggtgccac agcgtaagtt cgctgtggca cctgcacgtt g         51

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccacgctgtg gcacctgcac gtagactcgt gcaggtgcca cagcgaactt a         51

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgggtgcgtg caggtgccac agcggcctag cgctgtggca cctgcacgtt g         51

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gttagatgga gatgtaattg atatgtgtga ggaatgat                        38

<210> SEQ ID NO 18
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gttccctgat ctttagcctt aatcattcct cacaacatct ccatctaac            49

```
<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
taaggctaaa gatcagggaa caccata                                           27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tatggtgttc cctgatcttt agcctta                                           27

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gttagatgga gatgttgtga ggaatgatta aggc                                   34

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gttccctgat ctttagcctt a                                                 21

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gttaagtttg gggtgagatg taattgatat gtgt                                   34

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acctcacaca tatcaattac atctc                                             25

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gagatgtaat tgatatgtgt                                                 20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tgagggtagt ggagtgagg                                                  19

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtagtggagt gaggtgagga cctgggggag tattgcggag gaaggt                    46

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccaggtcctc acctcactcc actaccctca                                      30

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gttaagtttg gggtgagatg tagtggagtg aggt                                 34

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
acctcacctc actccactac atctc                                           25

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gagatgtagt ggagtgaggt                                              20

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gttaagtttg gggtg                                                   15

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
catctcaccc caaacttaac                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tttttttttt tttttttttt                                              20

<210> SEQ ID NO 35
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gttagatgga gatgtaattg atatgtgtga ggaatgatta aggctaaaga tcagggaaca   60
ccata                                                              65

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gagtattgtt aagttcgctg tggcacctgc acgttg                            36

<210> SEQ ID NO 37
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caacgtgcag gtgccacagc gtggggtg                                              28
```

MOLECULAR DNA STRAND-DISPLACEMENT CONTROLLERS FOR DIRECTING MATERIAL EXPANSION

REFERENCE TO RELATED APPLICATIONS

This application is a 35 U.S.C. § 371 U.S. national entry of International Application PCT/US2019/014439, having an international filing date of Jan. 22, 2019, which claims the benefit of U.S. Provisional Application No. 62/620,669, filed Jan. 23, 2018, the content of each of the aforementioned applications is herein incorporated by reference in their entirety.

STATEMENT OF GOVERNMENTAL INTEREST

This invention was made with government support under grant no. W911NF-15-1-0490 awarded by Army/ARO, and grant no. 221874, awarded by Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on Jan. 13, 2018, is named P14821-02_SL.txt and is 9,060 bytes in size.

BACKGROUND OF THE INVENTION

To survive in diverse or changing conditions, cells and tissues change their shape or behavior in response to a broad array of biochemical stimuli. Molecular receptors detect stimuli and trigger signal transduction pathways that amplify and integrate incoming chemical information and then direct a response. The separation of the machinery for sensing, signal processing and actuation makes the complex adaptive responses of cells possible. Integrating information about multiple inputs allows cells to respond intelligently to complex input combinations, while amplification of input signals makes it possible for cells to trigger a response in which high concentration of molecules be activated or transformed such as cell migration, differentiation, or growth. This organization means that new cell function can be developed through the rewiring of signal transduction pathways to reconnect or add inputs and responses.

Analogous systems for signal processing within engineered materials could likewise allow materials to emulate the complex responsiveness of cells. Soft materials, in particular hydrogels, where molecular systems for sensing and actuation could operate in aqueous media, are particularly amenable to this approach. Stimulus-responsive hydrogels offer important advantages over traditional materials in terms of energy efficiency and can be used as membranes or in tissue engineering. Hydrogels that respond to a variety of biomolecules, including enzymes, antibodies, or nucleic acids have been developed. However, because these stimulus molecules must interact directly with the hydrogel network, stimulus concentrations that are much higher than physiological concentrations and are often impractical to provide synthetically are required to induce a response. Desired are stimulus-responsive engineered materials where large-scale material responses are mediated by molecular controllers that sense different low-concentration inputs, process and amplify them, and direct a response.

SUMMARY OF THE INVENTION

One embodiment of the present invention is a locked gel comprising a polymer including a nucleic acid cross link and a nucleic acid lock. The nucleic acid lock is in a locked conformation preventing the locked gel from reacting with other nucleic acid sequences.

Another embodiment of the present invention is a method of unlocking a locked gel comprising the steps of providing a locked gel of the present invention; adding a nucleic acid key to a locked gel of the present invention; and changing the nucleic acid lock into an unlocked conformation allowing the gel to react with other nucleic acid sequences. Nucleic acid keys of the present invention bind to the nucleic acid lock. Preferably, if there is 1 or more unit of nucleic acid key and the nucleic acid lock is in the range of 6 to 120 units in the locked gel, then the nucleic acid key changes the nucleic acid lock to an unlocked conformation. Alternatively, it has been demonstrated that if the nucleic acid key is below a total concentration of 1 unit of nucleic acid key and the nucleic acid lock is in the range of 121-1000 units in the locked gel, then the nucleic acid key is unable to change the nucleic acid lock to an unlocked conformation. A suitable concentration range of the nucleic acid key within a lock gel is in a concentration range of 1 nM to 500 nM, 10 nM to 400 nM, 100 nM to 300 nM, 50 nM to 150 nM, 50 nM to 100 nM, or 60 nM to 90 nM, as examples. Methods of the present invention may also include a helper that binds to the nucleic acid lock that is bound to the nucleic acid key that allows the nucleic acid key to react with further nucleic acid sequences. Suitable total concentration of a helper of the present invention in a gel of the present invention is in the range of 1-20 units of helper to 1 unit of the nucleic acid lock in the gel. A suitable concentration range of helper is in the range of 1 uM to 20 uM, 5 uM to 10 uM, or 10 uM to 20 uM, for example.

Another embodiment of the present invention is a method of unlocking a locked gel comprising the steps of providing a locked gel of the present invention further comprising an inactive nucleic acid key. Next step is adding a first trigger changing the inactive nucleic acid key into an active nucleic acid key that changes the nucleic acid lock into an unlocked conformation allowing the gel to react with other nucleic acid sequences. Methods of the present invention may also include a helper that binds to the nucleic acid lock that is bound to the active nucleic acid key that allows the active nucleic acid key to react with further nucleic acid sequences. Methods of the present invention may include a first trigger that binds to a first intermediate forming a modified first intermediate and the modified first intermediate binds to the inactive nucleic acid key forming an active nucleic acid key. One example of a first intermediate is an aptamer, though most nucleic acid sequences may be used. Methods of the present invention may include a first trigger that binds to a first intermediate forming a modified first intermediate and the modified first intermediate binds to a second intermediate forming a modified second intermediate. The modified second intermediate binds to the inactive nucleic acid key forming an active nucleic acid key. Methods of the present invention may include third, fourth, fifth, or more intermediates. Methods of the present invention may include a first intermediate having a total concentration of 1 or more units and the nucleic acid lock having a total concentration in the range of 6 to 120 units in a gel of the present invention, as an example.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

"Active nucleic acid key" means a nucleic acid sequence that is able to bind to a nucleic acid lock and change it from a locked conformation to an unlocked conformation.

"Fragment" means a portion of a nucleic acid molecule. This portion contains, preferably, at least 10%, 20%, 30%, 40%, 50%, 60%, 70%, 80%, 85%, 90%, 95%, or 97% of the entire length of the reference nucleic acid molecule. A fragment may contain 3, 5, 10, 20, 30, 40, 50, 60, 70, 80, 90, or 100, 200, 300, 400, 500, 600, 700, 800, 900, or 1000 nucleotides or amino acids.

"Helper" means a nucleic acid sequence that is able to bind to a nucleic acid lock that is bound to a nucleic acid key and allow the key to bind other nucleic acid sequences.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

"Inactive nucleic acid key" means a nucleic acid sequence that is unable to bind to a nucleic acid lock.

"Locked Conformation" means when a nucleic acid lock prevents a locked gel from reacting with other nucleic acid sequences.

"Reference Sequence" means a defined sequence used as a basis for sequence comparison. A reference sequence may be a subset of or the entirety of a specified sequence; for example, a segment of a full-length cDNA or gene sequence, or the complete cDNA or gene sequence. For nucleic acids, the length of the reference nucleic acid sequence will generally be at least about 3 nucleotides, at least about 5 nucleotides, at least about 7 nucleotides, or even greater than about 10 nucleotides or any integer thereabout or therebetween.

"Specifically binds" means a nucleic acid sequences and binds a complementary nucleic acid sequence, but which does not substantially recognize and bind other molecules in a sample, for example, a biological sample, which naturally includes other nucleic acid sequences of the invention.

"Unlocked Conformation" means when a nucleic acid lock allows a locked gel to react with other nucleic acid sequence.

By "hybridize" means to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about $30°$ C., more preferably of at least about $37°$ C., and most preferably of at least about $42°$ C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at $30°$ C. in 750 mM NaCl, 75 mM trisodium citrate, and 1% SDS. In a more preferred embodiment, hybridization will occur at $37°$ C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at $42°$ C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about $25°$ C., more preferably of at least about $42°$ C., and even more preferably of at least about $68°$ C. In a preferred embodiment, wash steps will occur at $25°$ C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at $68°$ C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a nucleic acid molecule exhibiting at least 50% identity to a reference nucleic acid sequence (for example, any one of the nucleic acid sequences described herein). Preferably, such a sequence is at least 60%, more preferably 80% or 85%, and more preferably 90%, 95% or even 99% identical at the nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

BRIEF DESCRIPTION OF THE DRAWINGS

FIG. 2A-2C: Hydrogel particle synthesis and unlocking. (a) Hydrogel particles are prepared by pipetting droplets of pre-polymer acrylamide-DNA crosslinker solution into mineral oil and polymerizing the droplets with UV light. Rhodamine-B is incorporated into the acrylamide backbone to allow fluorescence imaging of particles (see Methods). (b) Fluorescence micrographs of particles. Particles without locks swell when hairpin fuel is added, but particles with locked crosslinks show less than 4% change in area over 70 hours (FIG. 10). Addition of Key strands to locked particles allows swelling. Scale bars: 500 (c) The change in area of the 2D projection of each particle over time for different concentrations of Key strand added at time 0. Curves are the average of 2 particles; shaded regions show 95% confidence intervals as determined by standard deviation.

FIG. 3A-3B: Catalytic crosslink unlocking enables a trigger at concentrations of 100 nM or less to trigger fast, high-degree swelling. (a) A Catalyst strand unlocks a crosslink via toehold-mediated strand-displacement to form an intermediate complex, which is unlocked. A Helper strand reacts with this intermediate to release the Catalyst strand, allowing it to unlock another crosslink. (b) Expansion in response to different concentrations of Catalyst and 10 µM Helper strands added to locked particles pre-incubated with DNA hairpins. Helper strands unlock crosslinks without Catalyst, but much more slowly than with Catalyst. Curves are the average of 2-4 particles with shaded regions representing 95% confidence intervals as determined by standard deviation.

FIG. 19A-19B: (a) Increasing the concentration of the aptasensor circuit components (Catalyst Source, ATP Sensor, and Cofactor strand) to 200 nM from 100 nM (FIG. 18) decreases the sensitivity of the swelling process to ATP concentration, perhaps because at higher concentrations circuit components can react with one another via unintended pathways at faster rates and thus produce more swelling in the off state. (b) The presence of Catalyst Source and ATP Sensor complexes ($S_{Cat}$ and $S_{ATPapt}$) or Cofactor at 200 nM increases the rate of swelling over the amount of observed in the presence of the Helper strand alone, even in the absence of ATP. Such an increase was not seen in the presence of 100 nM of the same circuit components (FIG. 18).

FIG. 20: Schematic of the components of the Logic Circuit. The circuit is based on a design from Seelig et al. The toehold, w, was designed to have minimal nonspecific crosstalk with all other sequences using NUPACK. The sequence for domain 7 is from Qian and Winfree. Figure discloses SEQ ID NOS 21, 20, 35, 18, 17, 23, and 24, respectively, in order of appearance.

DETAILED DESCRIPTION OF THE INVENTION

Figures 1A, 1B, 1C, 1D:
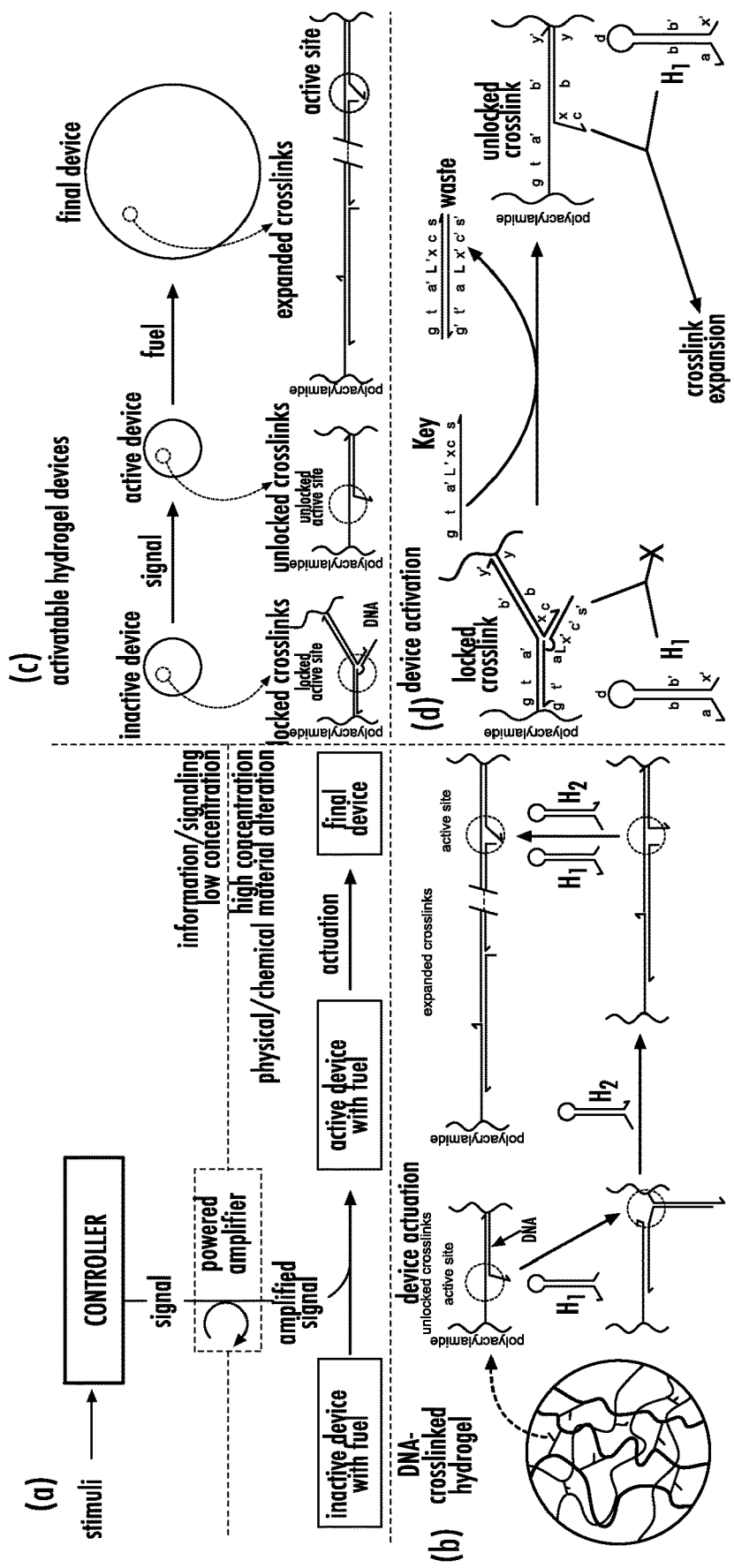
FIG 1A-D: Scheme for controlled expansion of DNA-crosslinked hydrogels gated by molecular signals. Colors within DNA strands show sequence domains, drawn to scale; complementary regions are shown in the same color. (a) Device architecture. A controller interprets stimuli and makes a decision about whether to switch the device from an inactive to an active state. The controller takes low-concentration inputs and processes them with low-concentration molecular circuit elements; the output is then amplified to produce high concentrations of molecules needed to activate high concentration crosslinks that interact with high-concentration fuel to drive material change. (b) DNA-crosslinked hydrogel architecture. Hybridized DNA oligonucleotides crosslink polyacrylamide chains. Schematic of the hairpin monomer incorporation that drives size change. Two types of hairpin monomers are inserted into crosslinks in alternating series at a single active site. (c) Control is achieved through activation a device through crosslink unlocking. Unlocked crosslinks can extend by incorporating hairpin fuel. (d) Crosslink unlocking by a Key strand through strand-displacement.

The present invention builds modular, material controllers that combine amplification with logic, translation of input signals and response tuning to directly and precisely program the dramatic material size change. Within the present invention, a programmable chemical controller decides whether to produce an output signal that is then amplified to produce a high-concentration actuation signal. This signal directs the material to use a separate supply of chemical fuel to induce size change (FIG. 1a). The present invention thus has a modular controller, actuator and energy source to program mechanical work, making it a primitive soft robot in which all parts are implemented as autonomous biochemical processes.

DNA-Crosslinked Hydrogels as State-Switchable Devices

The inventors began with a DNA-crosslinked polyacrylamide hydrogel as the material substrate (FIG. 1b). DNA-crosslinked hydrogels can respond to temperature, ions, nucleic acids, and small molecules by de-hybridizing, stiffening or softening the crosslinks, leading to shape-change or changes in elastic modulus. Recently, it was shown that DNA hairpins incorporating into the crosslinks could trigger up to 100-fold volumetric expansion of DNA crosslinked hydrogels. (FIG. 1b). The inventors hypothesized that upstream DNA circuits such as amplifiers, translators, or logic circuits could release DNA outputs that might direct this expansion. These circuits could in turn take as inputs different types or concentrations of chemical stimuli.

The inventors modified the hydrogel crosslinks so that they could be either in an active state, where DNA hairpins direct hydrogel expansion, or an inactive state, where crosslinks are unable to interact with hairpins (FIG. 1c,d). Crosslinks can switch from an inactive to active state via a toehold-mediated DNA strand-displacement process (FIG. 1d). The strand that unlocks the crosslink is a short, single-stranded DNA strand of a form that can be the output of DNA strand-displacement logic or sensing circuits.

DNA-Crosslinked Hydrogel Particles as a Model Swelling System

Figures 5A, 5B:
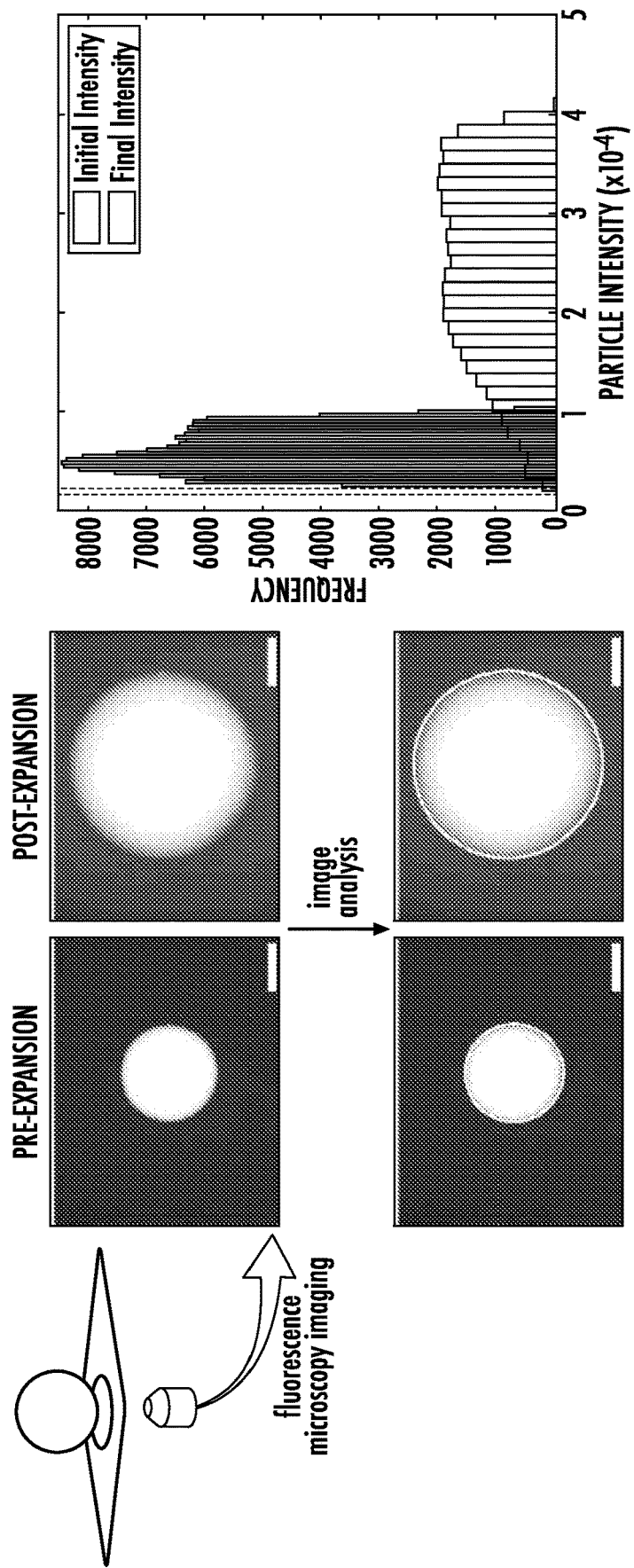
FIG. 5A-5B: Measuring the area and intensity of a particle's 2D fluorescence projection. (a) Particles were imaged using fluorescence microscopy and the area of the particle as seen in the 2D micrograph was determined using MATLAB. The green line around each particle in the bottom images represent the calculated boundary of each particle. The area of the pixels within this boundary is the calculated particle projection area. Image intensities are scaled based on each image's minimum and maximum intensity. Scale bars are 500 µm. (b) Histogram of the intensity of the right particle (pixels within the green boundary) shown in (a). As the particle expands, the intensity of the particle decreases because the density of rhodamine fluorophores decreases.
Figure 6:
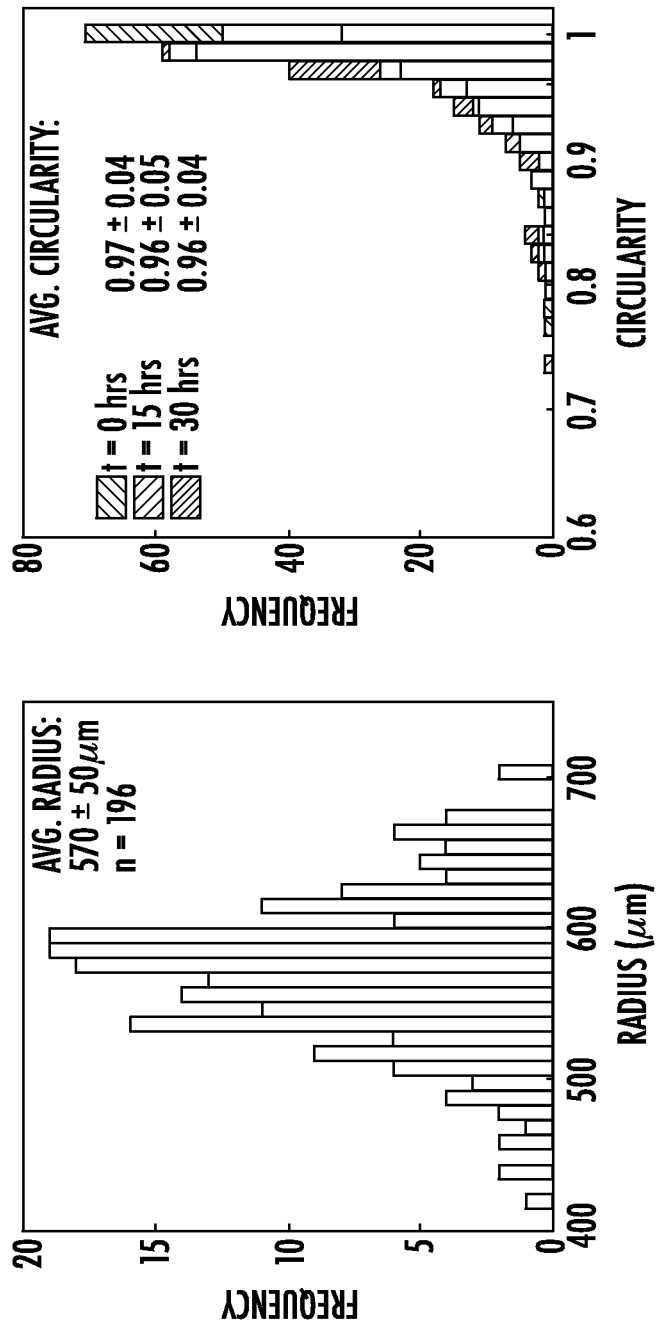
FIG. 6: Average radii and circularity of DNA-crosslinked hydrogel particles before expansion. (a) Distribution of Rhodamine-labeled poly(DNA-co-acrylamide) particle radii was determined. (b) Circularity scores of particles before expansion (N=196). A particle with a circularity score of 1 is a perfect circle. The mean circularity is 0.97±0.04 at time 0 and 0.96±0.04 after 30 hours of incubation with hairpins. These statistics are derived from the particles used in the studies in this experiment, so particles that expand to different extends are included in these time averages.

The inventors characterized swelling kinetics using hydrogel spheres synthesized in a droplet-based photo polymerization process that they developed (see Methods and FIG. 2a). Spheres expand evenly, so that swelling kinetics can be measured reliably by measuring changes in their radius or area. The inventors measured particle size as the area of a particle's 2D projection in fluorescence micrographs (FIG. 5). The average radius of synthesized particles after equilibration in buffer was 570±50 µm (Methods). The projections of 93.4% of particles were at least 90% circular (FIG. 6).

Figure 7:
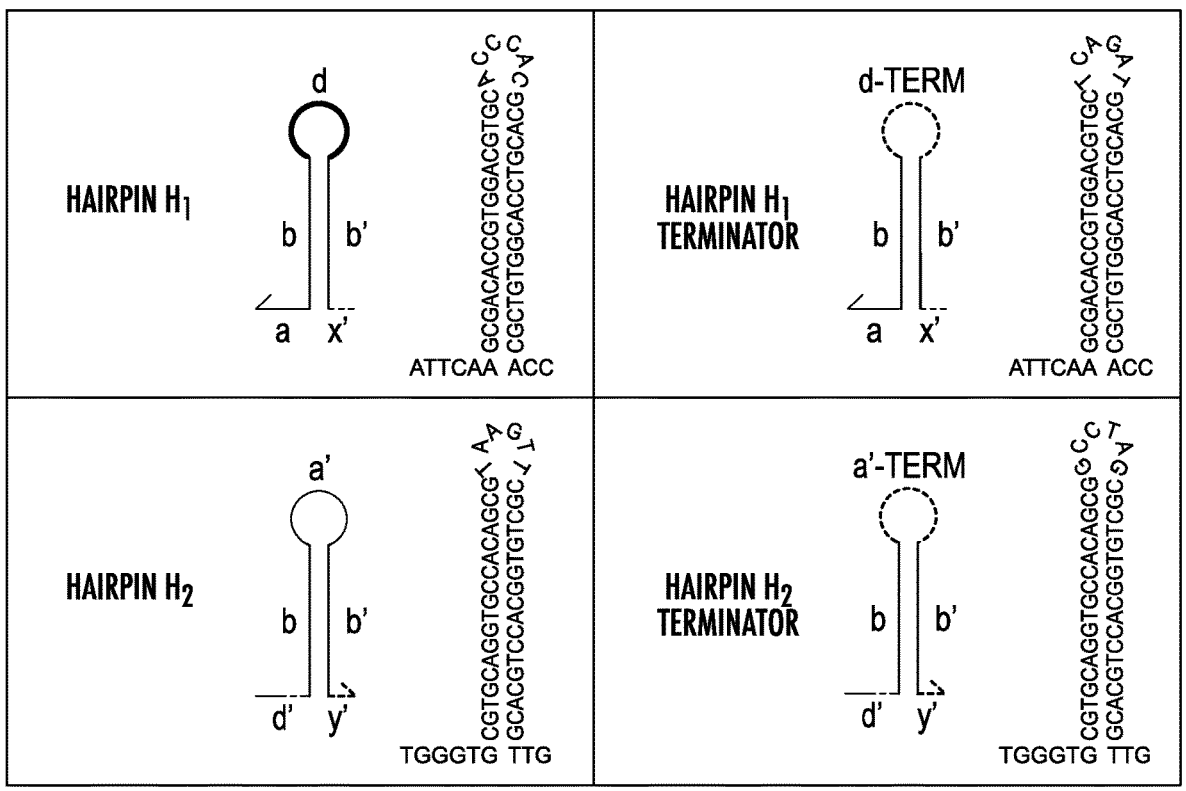
FIG. 7: DNA hairpin monomer sequences. Terminator hairpins share the same sequence as their non-terminator counterpart except for the loop region so that after insertion of a terminator hairpin, other hairpins cannot insert into the crosslink. Figure discloses SEQ ID NOS 13, 15, 14, and 16, respectively, in order of appearance.
Figure 8:
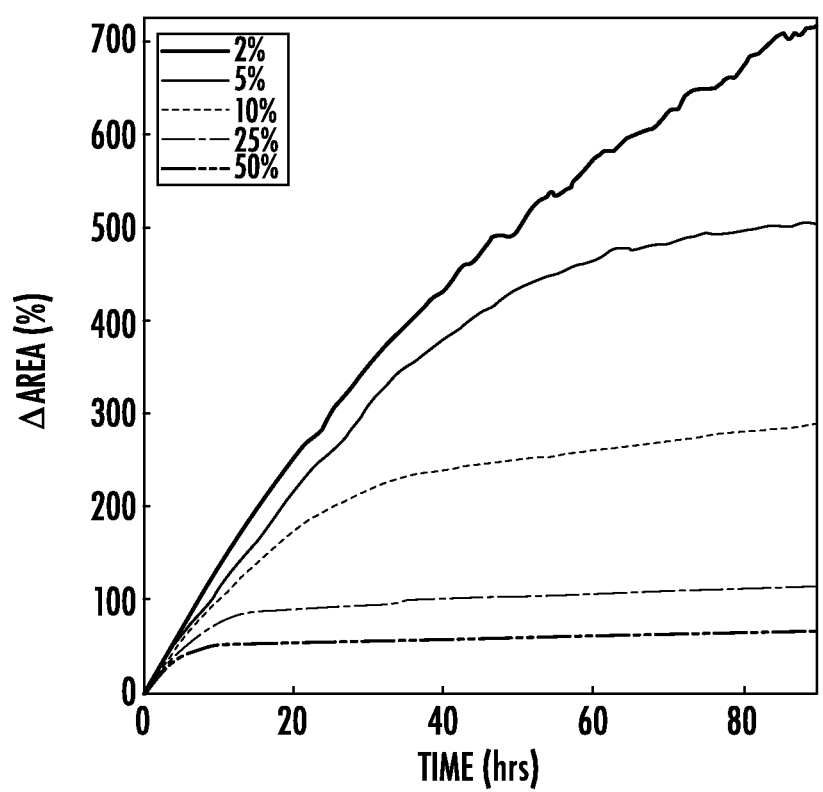
FIG. 8: Effect of the proportion of hairpins that are terminator hairpins on the swelling of DNA-crosslink hydrogels without locks. Particles without locks were incubated with DNA hairpins at 20 µM total per type, such that the fraction of hairpin terminator of each type was different in each sample. Each curve represents 1 particle or the average of 2 particles.
Figure 9:
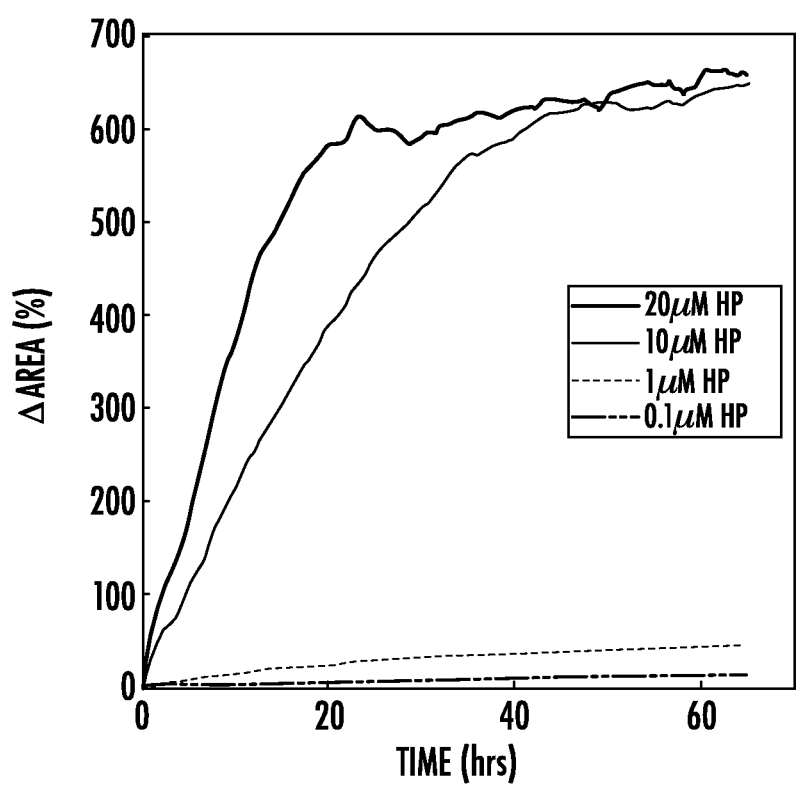
FIG. 9: Particles prepared without crosslink locks incubated with different concentrations of hairpin (concentration per type is shown). In all cases, the percentage of terminator hairpin is 10%.

The inventors first verified that hydrogel particles synthesized with active crosslinks (i.e. without locks) swell in the presence of their corresponding DNA fuel, a mixture of polymerizing and terminating monomers (FIG. 1b, FIG. 7). Both monomer types can insert into crosslinks; after incorporation, polymerizing monomers present a site a where subsequent monomers can insert, while terminating monomers do not. Particles swelled at a roughly constant initial rate, then more slowly as they approached a final size (FIG. 2b, FIG. 8). The fluorescence intensity of the hydrogels decreased as their sizes increased due to decreasing Rhodamine density (FIG. 2b, FIG. 5). The intensity of the particles also became non-uniform during swelling, suggesting swelling occurred first near the particle surface then in the center (FIG. 2b). The swelling rate and final size could be tuned across a wide range by adjusting the monomer concentration or the fraction of monomers that were terminating (FIGS. 8-9). To compare the influence of locks and controllers on a standard swelling process, in subsequent experiments the inventors used 20 µM of each monomer of which 10% were terminators.

Activating Particles with Key Strands

Figure 10:
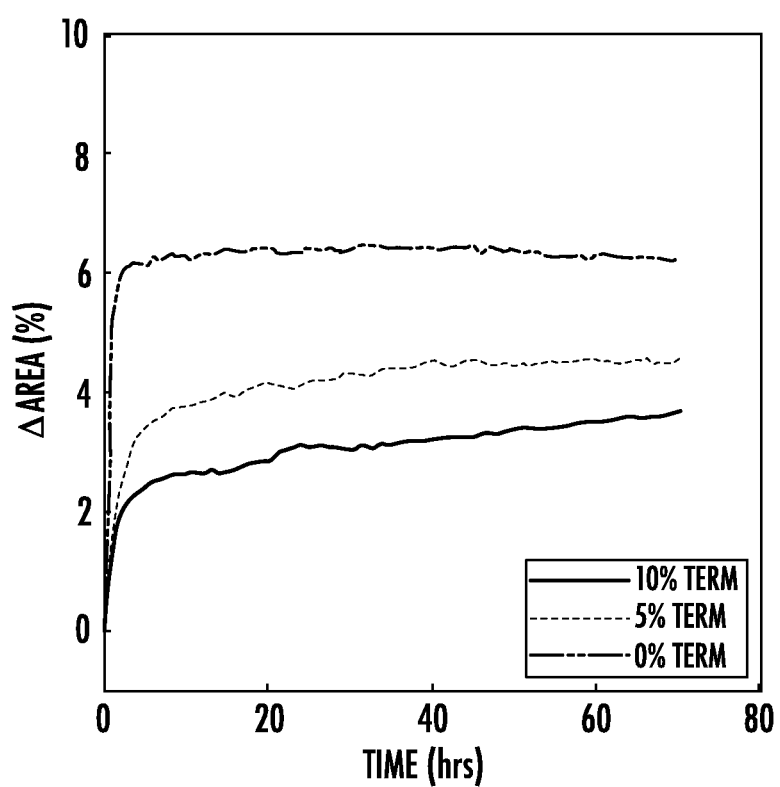
FIG. 10: Locked crosslink hydrogel particles show 50-fold less swelling than hydrogels with no locks. Swelling was tested with different percentages of hairpin terminator over 70 hours and 20 µM per hairpin type. Each curve is the average of two particles.
Figure 11:
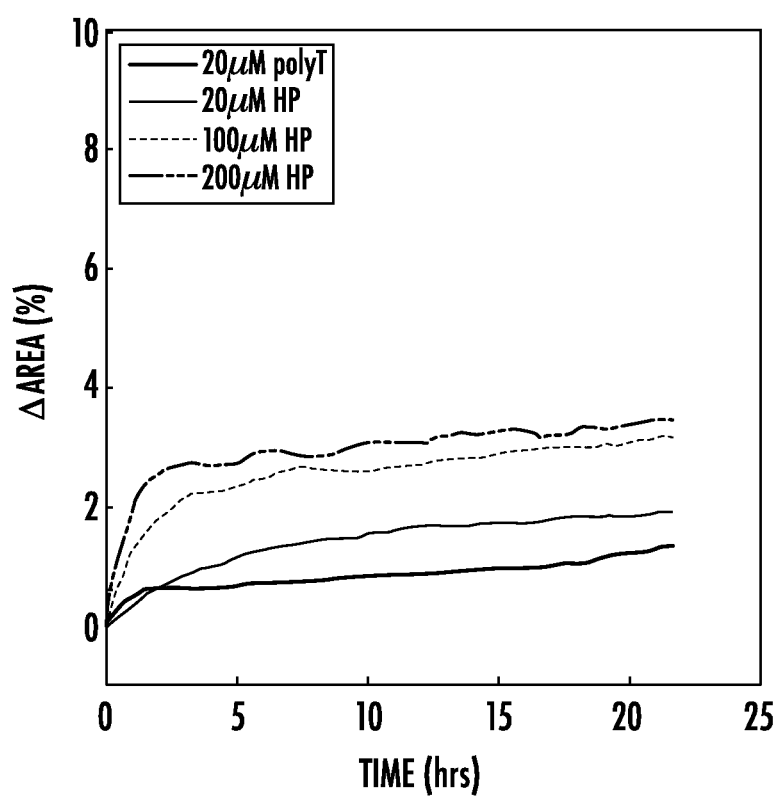
FIG. 11: Swelling of locked particles incubated with different concentrations of hairpins or a 20-mer of thymine (polyT) (SEQ ID NO: 34). In all cases, the fraction of hairpin terminator is 10%. Curves are the average of 2-4 particles.

When hydrogel particles with locked crosslinks were incubated with hairpin fuel, only a 3.7±4.5% in area was observed over 60 hours, as compared to 260±2% for crosslinks without locks (FIG. 2b, FIG. 10). Most swelling of locked particles occurred in the first 5 hours. Increasing the hairpin concentration to 200 µM did not increase the locked particles swelled (FIG. 11). Thus, fuel does not trigger significant expansion of a hydrogel with locked crosslinks.

The inventors next tested whether adding a Key strand that can unlock crosslinks (FIG. 1d), could allow the particles to expand in the presence of fuel. The inventors first incubated the locked particles with fuel for 24 hours to allow the fuel monomers to diffuse into the particles, then added different concentrations of Key strand to different particles. Key strands induced swelling (FIG. 2b) and particles swelled more in the presence of higher Key strand concentrations (FIG. 2c). This is consistent with increases in swelling observed with increasing fractions of active (vs. inactive) crosslinks.

Activating Particles Through Catalytic Crosslink Unlocking

While Key strands trigger swelling, the Key concentrations required are higher than the 1 nM to 1 µM typical for the outputs of DNA strand-displacement processes, so making a circuit that produced a Key as the output to control swelling would require new approaches. Generally, the ability to induce swelling in response to low concentrations of a trigger molecular would also mean that smaller concentrations of the molecular circuit components could also be used, making it much more practical to implement complex processing systems requiring many different species.

The inventors thus designed a molecular amplification process to allow one input strand to unlock many crosslinks. The inventors based their design on catalytic DNA strand-displacement circuits where an input strand first triggers the release of an output and is then released by a helper molecule that is consumed in the reaction. These catalytic circuits can amplify the input signal 100-100,000-fold.

In the catalytic crosslink unlocking process of the present invention, the Key strand is replaced by Catalyst and Helper strands (FIG. 3a). The Catalyst strand can bind to a crosslink and partially release the lock. The Helper strand can then bind to the Catalyst-crosslink complex, producing an unlocked crosslink and a waste complex, while the Catalyst is released to unlock another crosslink. Thus, in the presence of a larger Helper concentration, a small concentration of Catalyst activates the device.

Figure 12:
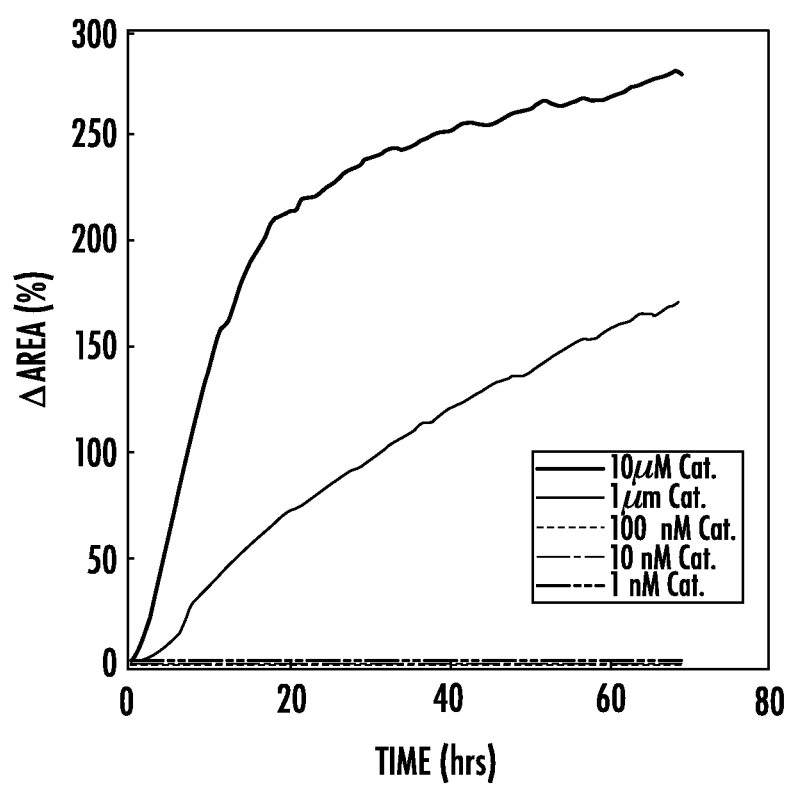
FIG. 12: Swelling of locked particles with hairpin fuel and different concentrations of Catalyst strand. The rate of swelling increases with increasing Catalyst concentration. Hairpins are 20 µM per type with 10% terminator. Curves for 1, 10, and 100 nM Catalyst are indistinguishable from one another. Curves are the average of two particles.

Without the Helper strand, a Catalyst strand should still be able to unlock one crosslink, but will not be released after unlocking (FIG. 3a). Therefore, in the absence of Helper the Catalyst should work like the Key strand, producing roughly the same amount of swelling at the same concentrations. Indeed, the inventors observed that 10 µM of Catalyst was needed to achieve the same high-degree change in area of 270±1% over 60 hours seen in response to 10 µM of Key strand. Over the same time period, less than a 2% increase in area was observed at Catalyst concentrations of 100 nM or less (FIG. 12).

Figure 13:
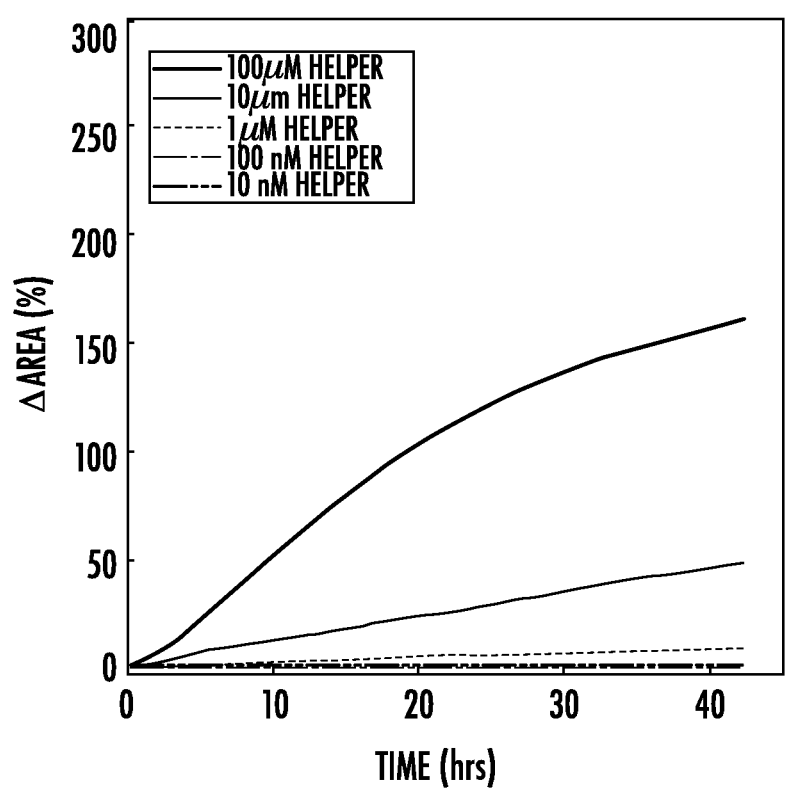
FIG. 13: Swelling of locked particles with hairpin fuel and different concentrations of Helper strand. Hairpins are 20 µM per type with 10% terminator. Curves are the average of two particles.

Because there is no toehold where the Helper and locked crosslink can bind to initiate fast displacement of the crosslink lock, little to no unlocking (and thus expansion) should occur in the presence of Helper strand and fuel but no Catalyst. As expected, locked hydrogel particles incubated with Helper strands and fuel expanded just 8±2% after 40 hours at Helper concentrations of 1 μM or below (FIG. 13). At 10 μM of Helper strand, 47±4% expansion was observed after 40 hours, which is significant but still well below the 200-250% increase in area observed in response to 10 μM of Key or Catalyst over the same time period (FIG. 2d, FIG. 12).

Figure 14:
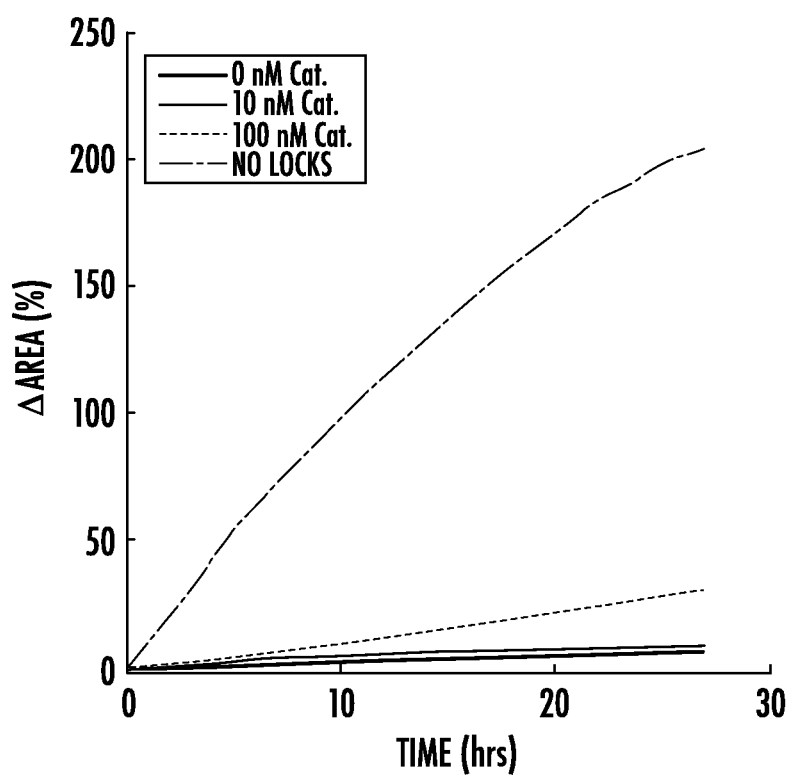
FIG. 14: Swelling rates of locked hydrogel particles in the presence of hairpins, 1 µM Helper and different concentrations of Catalyst. The amount of swelling observed over 25 hours is much less than the swelling observed when 10 µM Helper rather than 1 µM is present (FIG. 15), indicating that a higher Helper concentration is needed for high catalytic turnover and high-degrees of swelling. The swelling of particles prepared without locks is shown for comparison. The hairpin concentration for all curves is 20 µM per type with 10% terminator. Curves are the averages of measurements from 2-6 particles.
Figure 15:
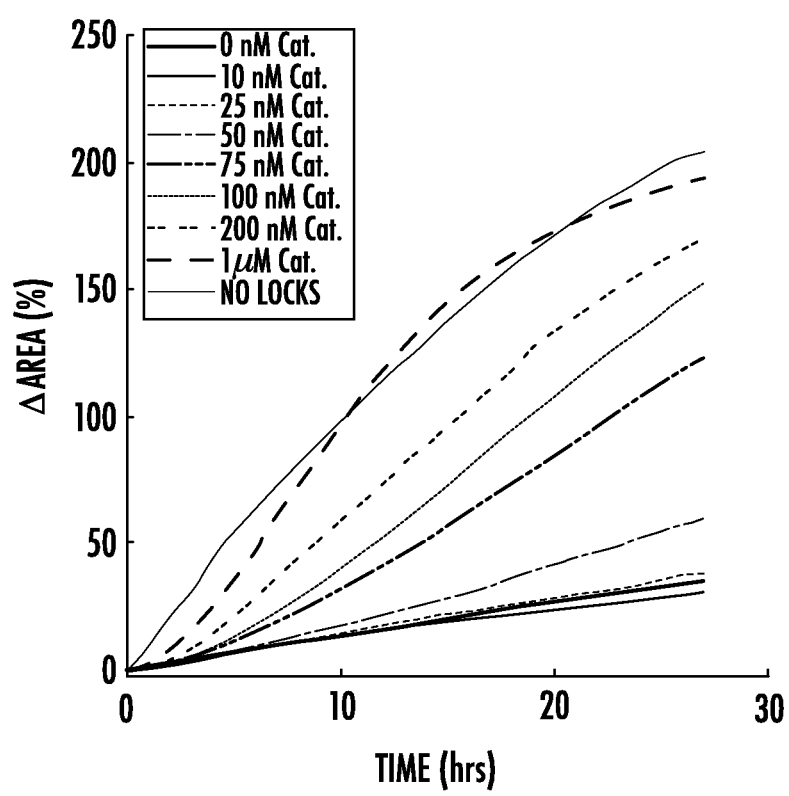
FIG. 15: Swelling rates for 10 µM Helper and different concentrations of Catalyst. The swelling of particles prepared without locks is shown for comparison. The hairpin concentration for all curves is 20 µM per type with 10% terminator. Curves are the averages of measurements from 2-6 particles.

In contrast, when as little as 100 nM Catalyst was added to the 10 μM Helper and hairpin fuel (FIG. 3b), particles expanded as fast as particles without locks. Larger concentrations of Catalyst strand did not significantly increase the extent of swelling, consistent with the idea that Catalyst strands are each capable of initiating multiple unlocking reactions. The high concentration of Helper is also critical to expansion: particles expanded 5-fold less in the first 24 hours in response to 100 nM Catalyst and 1 μM Helper than in response to 100 nM Catalyst and 10 μM Helper (FIG. 3b, FIG. 14). At high Helper strand concentrations, the concentration of Catalyst controlled how quickly swelling began (FIG. 15). This observation is consistent with the idea that when Catalyst concentrations are small, significant Catalyst turnover is required before most crosslinks have been unlocked.

Figures 4A, 4B, 4C, 4D, 4E, 4F:
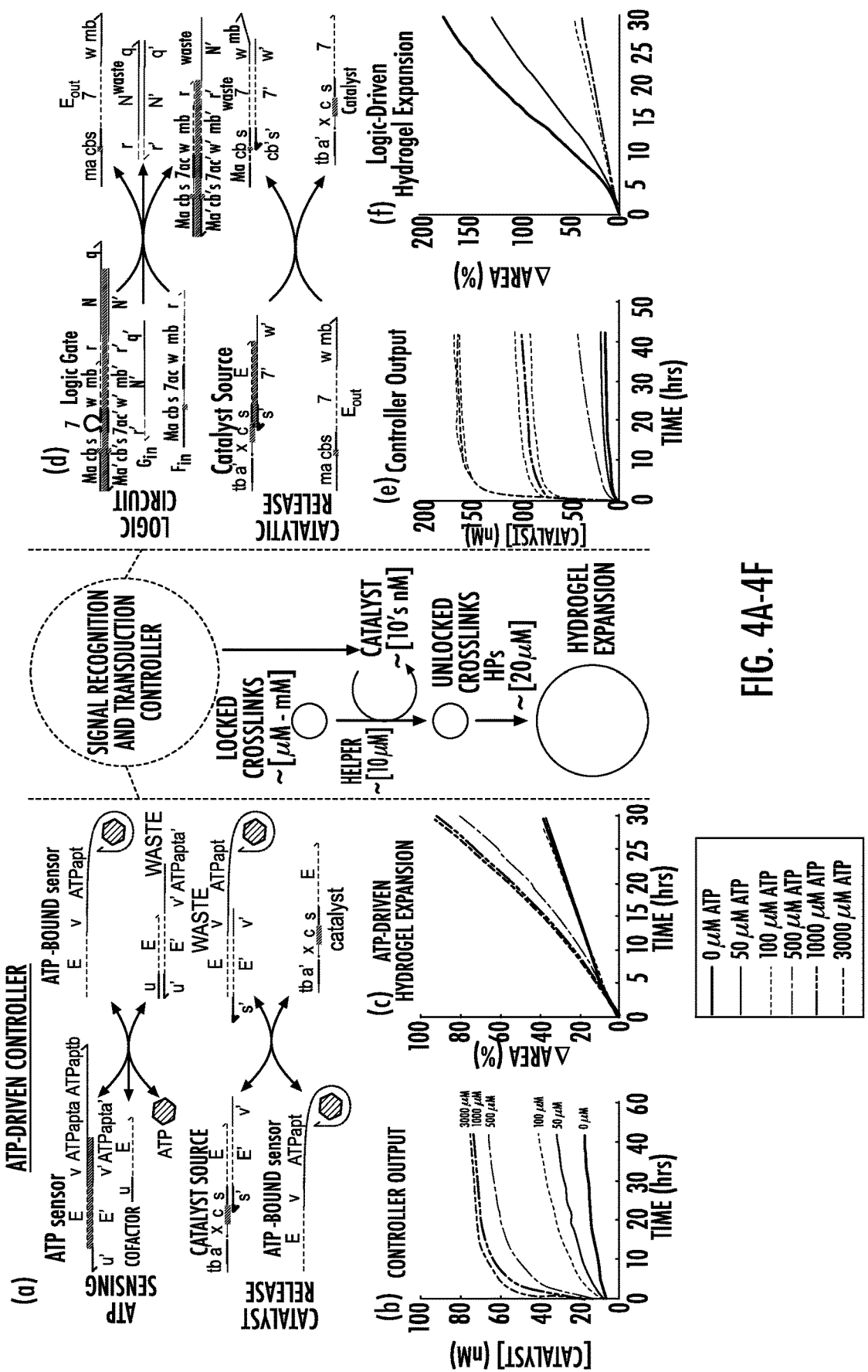
FIG. 4A-4F: Controllers that direct hydrogel expansion in response to different types of chemical inputs. (a) An aptamer-containing strand-displacement circuit that releases Catalyst in response to ATP. (b) Solution kinetics of the circuit in (a) measured using fluorescence reporting (see Methods, FIG. 17) in response to different ATP concentrations. ATP sensor, Cofactor, and Catalyst Source initially at 100 nM. (c) ATP-controlled rates of particle swelling mediated by the circuit in (a), catalytic crosslink unlocking (FIG. 3a) and hairpin-polymerization (FIG. 1b). Sensor, Cofactor, and Catalyst Source at 100 nM; Helper strand at 10 µM. (d) DNA strand-displacement AND logic circuit. Two inputs, $F_{in}$ and $G_{in}$, are required for Catalyst release. (e) Kinetics of the logic circuit in (d) in solution measured by fluorescence reporting. The logic gate and Catalyst Source at 200 nM. (0 Particle expansion in the presence of different $F_{in}$ and $G_{in}$ concentrations. Logic gate and Catalyst Source at 200 nM; Helper at 10 µM. N=3 (b, e) or 2-6 (c, 0. Shaded regions represent 95% confidence intervals determined by standard deviation.
Figure 16:
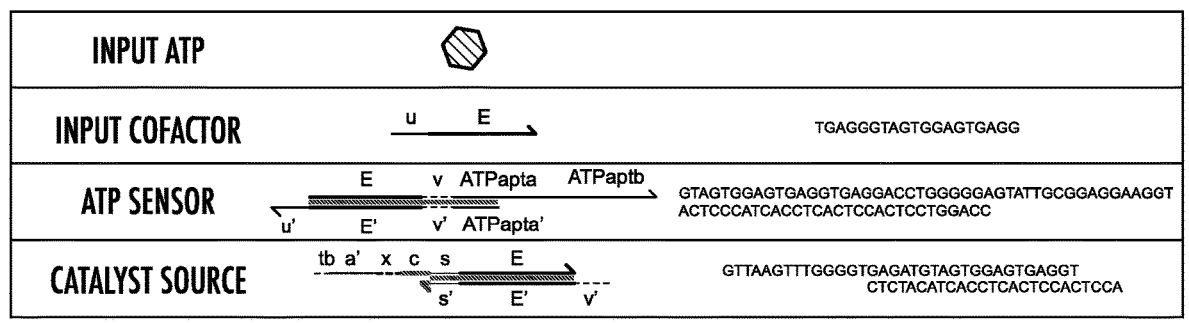
FIG. 16: Components of the ATP aptasensor circuit. ATPapta and ATPaptb (dark green domain) are the domains containing the ATP aptamer sequence. The toeholds u and v and domain E were designed to have minimal nonspecific crosstalk with all other sequences using NUPACK. Figure discloses SEQ ID NOS 26-30, respectively, in order of appearance.

Controllers for Directing Hydrogel Shape Change in Response to Small Molecule Inputs The inventors next asked whether they could couple molecular circuits to the catalytic unlocking process by designing DNA strand-displacement circuits that produced the Catalyst strand as an output. The inventors first designed an aptasensor circuit that releases a strand containing the Catalyst sequence only when ATP is present (FIG. 4a, FIG. 16). In the absence of ATP, the Catalyst sequence is partially sequestered in double-stranded form, preventing it from interacting with the hydrogel crosslinks. A Cofactor strand can bind the ATP-Sensor complex to separate the two strands of the complex. The ATP-bound sensor can then displace the Catalyst from the Catalyst source complex. This system of interactions ensures that Catalyst can be released at a significant rate only when ATP and the Cofactor are both present in solution.

Figure 17:
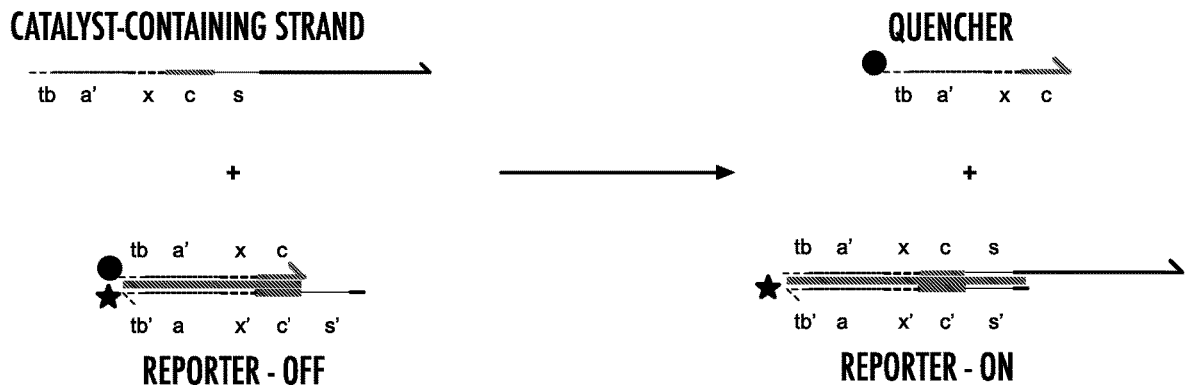
FIG. 17: Reporter reaction that detects the presence of exposed Catalyst sequence through an increase in fluorescence. Star is the FAM fluorophore, circle the IowaBlack quencher. The toehold on the Reporter is 5 bases (see Table 1 for sequences).

The inventors characterized the release of Catalyst in response to ATP in solution using a fluorophore-quencher reporting assay (Methods, FIG. 17). In the presence of 100 nM each of the ATP sensor complex, Catalyst source complex, and Cofactor, ATP triggered Catalyst release, with more ATP triggering more release (FIG. 4b). Catalyst concentrations of about 75 nM, the smallest concentration we observed that produced fast particle swelling, were produced only in response to ATP concentrations above 500 μM, while less than 40 nM Catalyst was produced at 100 μM ATP. When no ATP was present, some Catalyst was still produced, possibly due to the ability of a Cofactor-ATP sensor complex to react slowly with the Catalyst Source complex even in the absence of ATP.

Figure 18:
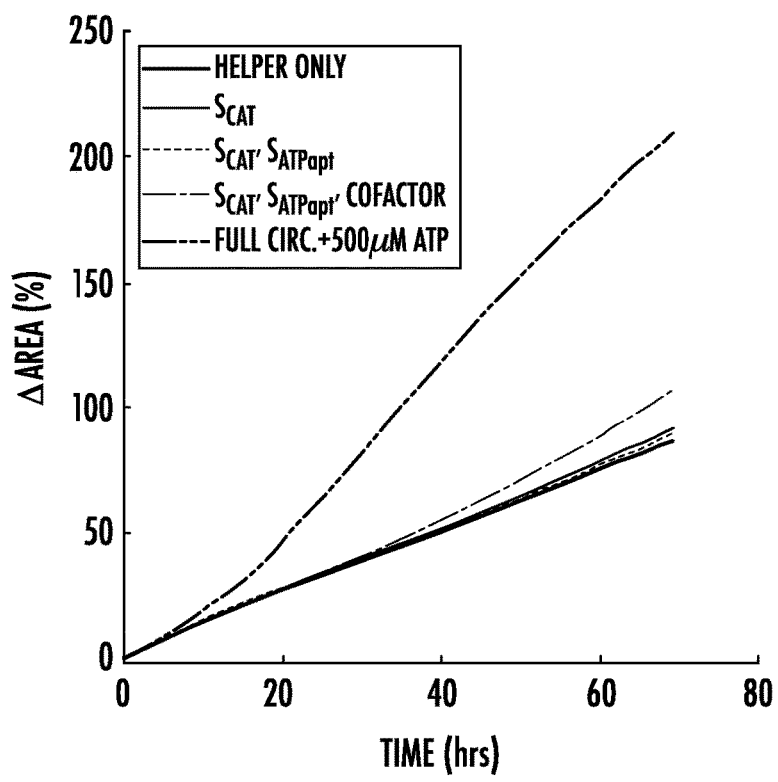
FIG. 18: Aptasensor circuit components (FIG. 16) do not significantly increase swelling in the absence of ATP. Particles incubated with Catalyst Source and ATP sensor complexes ($S_{Cat}$ and $S_{ATPapt}$) did not show more swelling than particles containing only 10 µM Helper strand. Slightly more swelling is observed when the cofactor is included than in other systems. The swelling of particles in the presence of the full circuit and 500 µM ATP is shown for comparison. Curves are the averages of 3-6 particles.

When locked hydrogel particles were incubated with the ATP-driven controller circuit, the amount of particle expansion depended on ATP concentration (FIG. 4c). Interestingly, the dose-response relationship between ATP concentration and particle swelling was somewhat digital. ATP concentrations below 500 μM did not significantly increase the rate of swelling over the baseline rate observed in response to 0 μM ATP, whereas swelling rates were similar for ATP concentrations of 500 μM and above. This behavior can be understood by convolving the responses of the controller and the circuit: the controller releases Catalyst concentrations that produce similar expansion rates at ATP concentrations above 500 μM and below 500 μM. Supporting this interpretation, we found that the Controller and the catalytic unlocking process and expansion appear modular—the addition of the ATP-sensing circuit (but no input) to the amplifier circuit, crosslink locks, and hairpin fuel did not change the swelling rate (FIG. 18). This modularity suggests that one could replace either the aptamer sensor or the crosslinks to trigger hydrogel expansion in response to different chemical inputs or to direct expansion of hydrogels with different crosslink sequences. However, because unintended interactions can occur at different concentrations of the DNA species (FIG. 19), designing and tuning the system as a whole to reduce such interactions may be required.

Triggering Hydrogel Actuation in Response to Input Combinations

The inventors next tested whether hydrogel expansion could be directed in response to specific combinations of multiple inputs, each presented at small concentrations. Previously, hydrogels have been engineered to change color, gel or swell slightly in response to logical combinations of inputs. However, in these systems, the inputs interacted directly with the crosslinks, limiting the range of potential chemical inputs and necessitating very input high concentrations to elicit the response. Our controller design circumvents these limitations. The controller can interpret input signals that do not interact with the material and in situ signal amplification within the controller makes it possible to direct changes in response to low (100-200 nM) input concentrations.

Figure 21A:
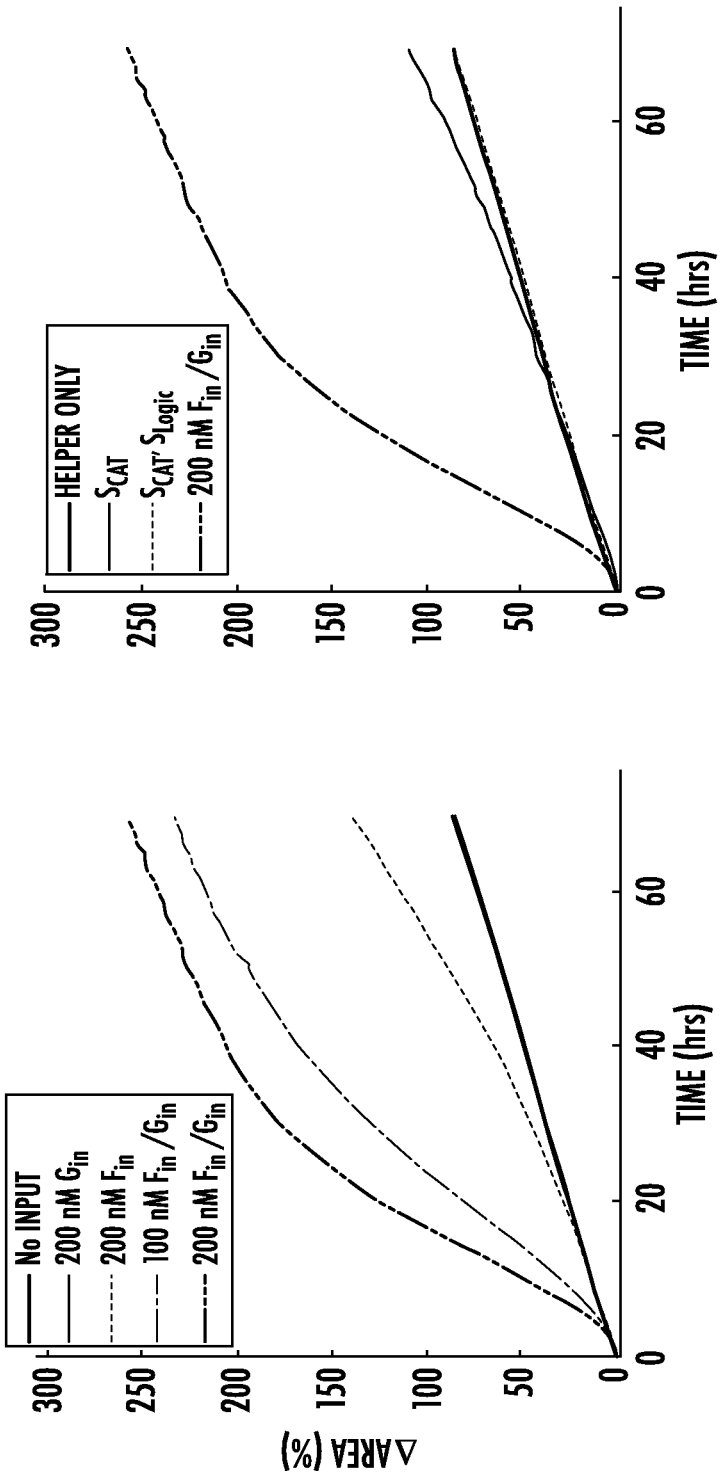
FIG. 21A-21B: Swelling kinetics of the particles when incubated with the Logic Circuit over 70 hours. (a) Results from the experiment in FIG. 4f of the Main Text shown over 70 (rather than 40) hours. (b) Particles swell no more in the presence of Catalyst Source and Logic gate complexes ($S_{Cat}$ and $S_{Logic}$) at 200 nM and no inputs than they do in the presence of the Helper strand but no circuit components.
Figure 21B:
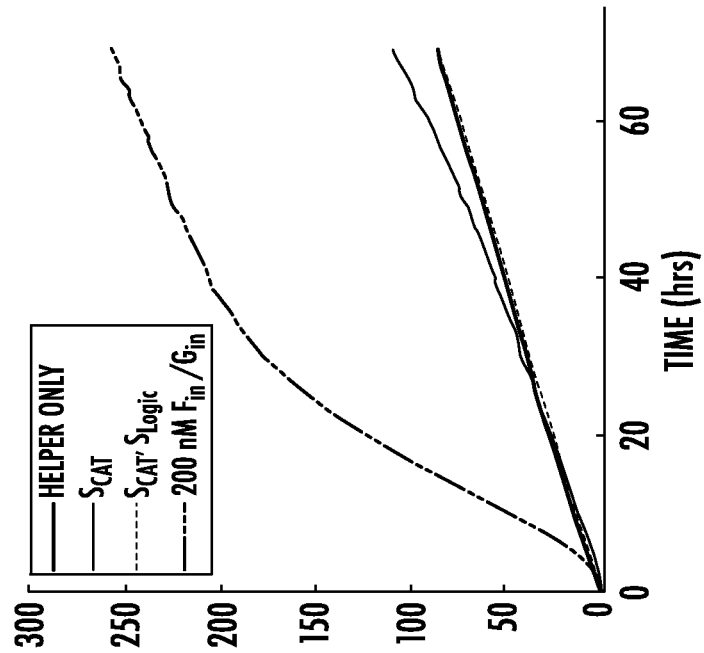

The inventors modified a previously developed DNA strand-displacement and logic circuit to release concentrations of Catalyst strand sufficient to trigger hydrogel expansion only when both inputs are present (FIG. 4d-e, FIG. 20). As designed, significant particle swelling occurred only in the presence of both inputs (FIG. 40. Without inputs, the addition of the circuit components did not increase the swelling rate, (FIG. 21), demonstrating that like the ATP-sensing controller, this controller operates modularly with respect to the amplification and unlocking processes. Some swelling was observed in response to input $F_{in}$ alone (FIG. 21a), perhaps due to sequence similarity between $F_{in}$ and the Catalyst, notably at toehold domains s and cb (FIG. 20). To better illustrate how logic can gate large-scale material change, the inventors organized movies of particles in the presence of different input combinations expanding into a swelling "truth table".

Interestingly, while the swelling behavior observed is digital, the controller does not contain a nonlinear threshold amplifier typically required for digital logic: the concentration of the output should simply be the minimum of the concentrations of the inputs. Digital behavior is observed because the catalytic expansion process performs the required nonlinear transformation. If the controller's output is above about 75 nM, catalytic amplification induces fast swelling, whereas for lower catalyst concentrations very little swelling occurs. Because DNA strand-displacement amplifiers, like the catalytic amplifier can produce output even in the off state due to undesired "leak" interactions between system components, the ability to operate without one likely improves the controller's reliability. This design also suggests how modular circuits coupled to material systems can exploit the behavior of the material itself for control to maximize both performance and system simplicity.

The inventors have shown how to use catalytic amplification of a small concentration of a trigger molecule to direct a dramatic change in material size, demonstrating systematically that engineered signaling processes between species at low concentrations can control the chemistry and behavior of dense materials which contain orders of magnitude more material and mass that must be transformed than the stimulus or the circuit. This system allows tens of nanomolar of an input signal to change the conformations of material components present at millimolar concentrations, an effective amplification factor of more than 10,000.

Figures 22A, 22B:
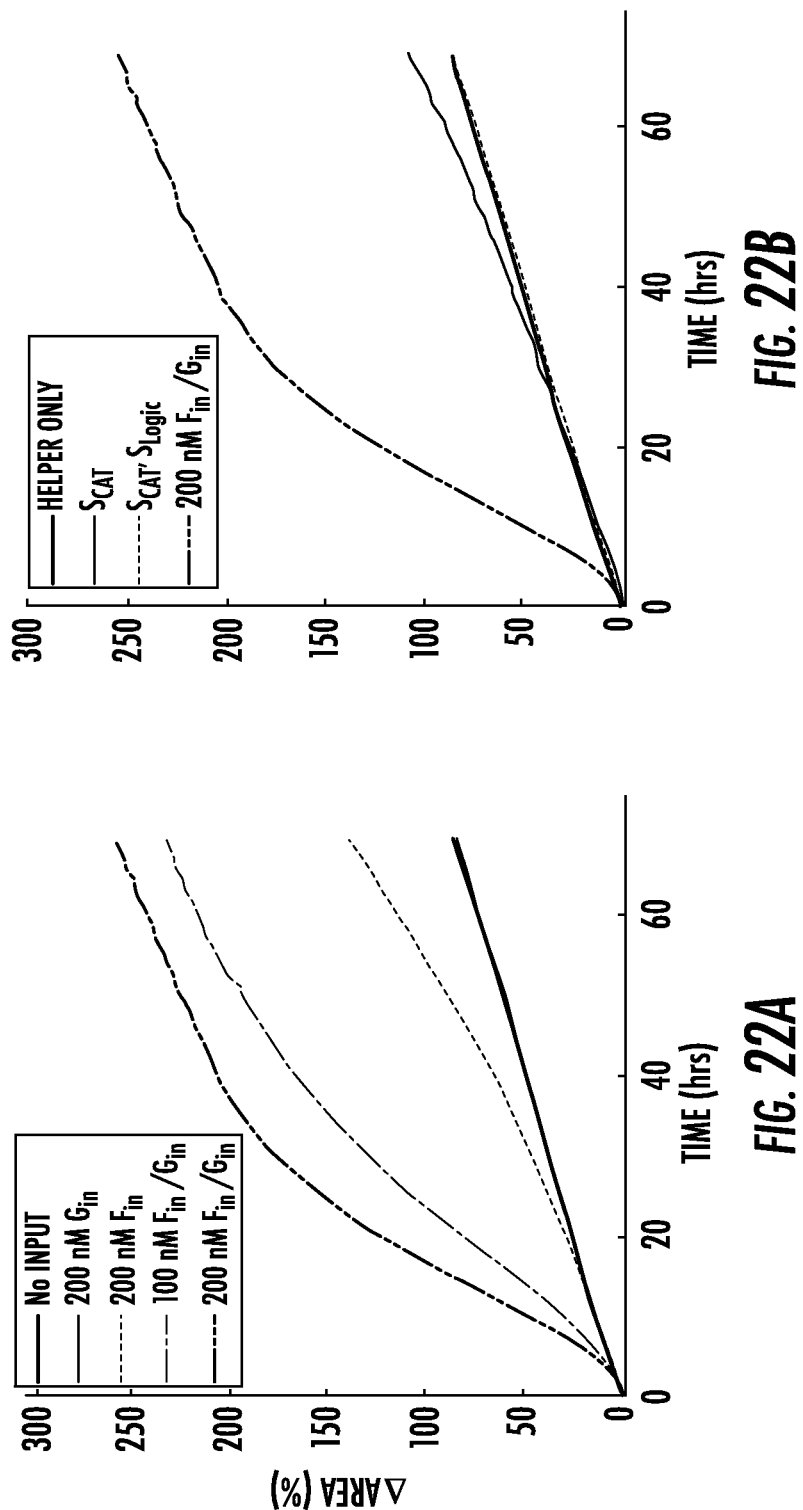
FIG. 22A-22B: Swelling of particles with 100 nM (a) or 10 nM (b) Catalyst and 10 µM Helper strands incubated with different concentrations of hairpin. Concentrations in the legends are "per hairpin type" of which 10% were termination hairpins. Curves are single particles (200 µM) or an average of 2-4 particles. When either 10 or 100 nM of Catalyst is present, very high concentrations of hairpins led to slower swelling. Higher hairpin concentrations would be expected to lead to faster swelling, because the rate of their incorporation at unlocked crosslinks should be faster than at lower concentrations. The decreased speed of swelling at higher concentrations of hairpin, could be due to sequestration of Catalyst and/or Helper strands by the hairpins, as their active site domains have complementary regions (FIGS. 7 and 24).
Figure 23:
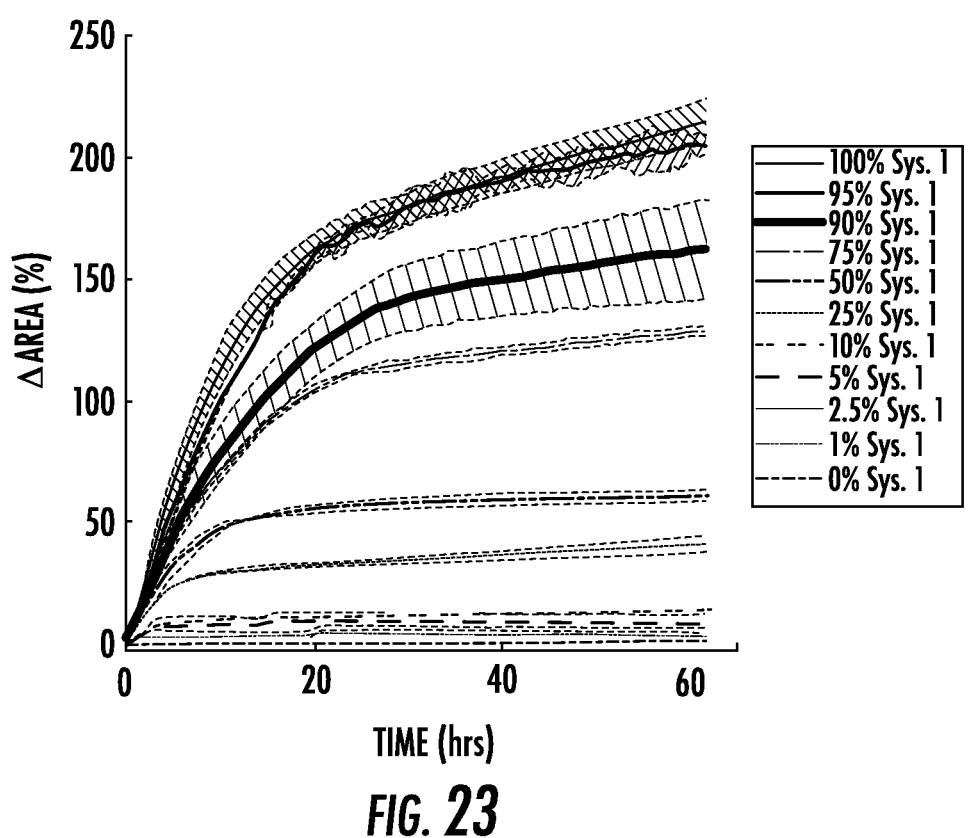
FIG. 23: Swelling kinetics of particles prepared with different fractions of expandable crosslinks (System 1) vs. crosslinks with different sequences designed to not interact with the Key strand or hairpins (System 2, sequences in Table 1). Particles were incubated with 20 µM hairpins of which 10% terminator hairpins. The legend gives the percentage of crosslinks that are expandable via hairpins. The curve for 100% System 1 crosslinks shows the average expansion of 8 particles. All other curves show the average expansion of 3 particles. Shaded regions surrounded by dashed lines show the region of 95% confidence as determined by standard deviation.
Figure 24:
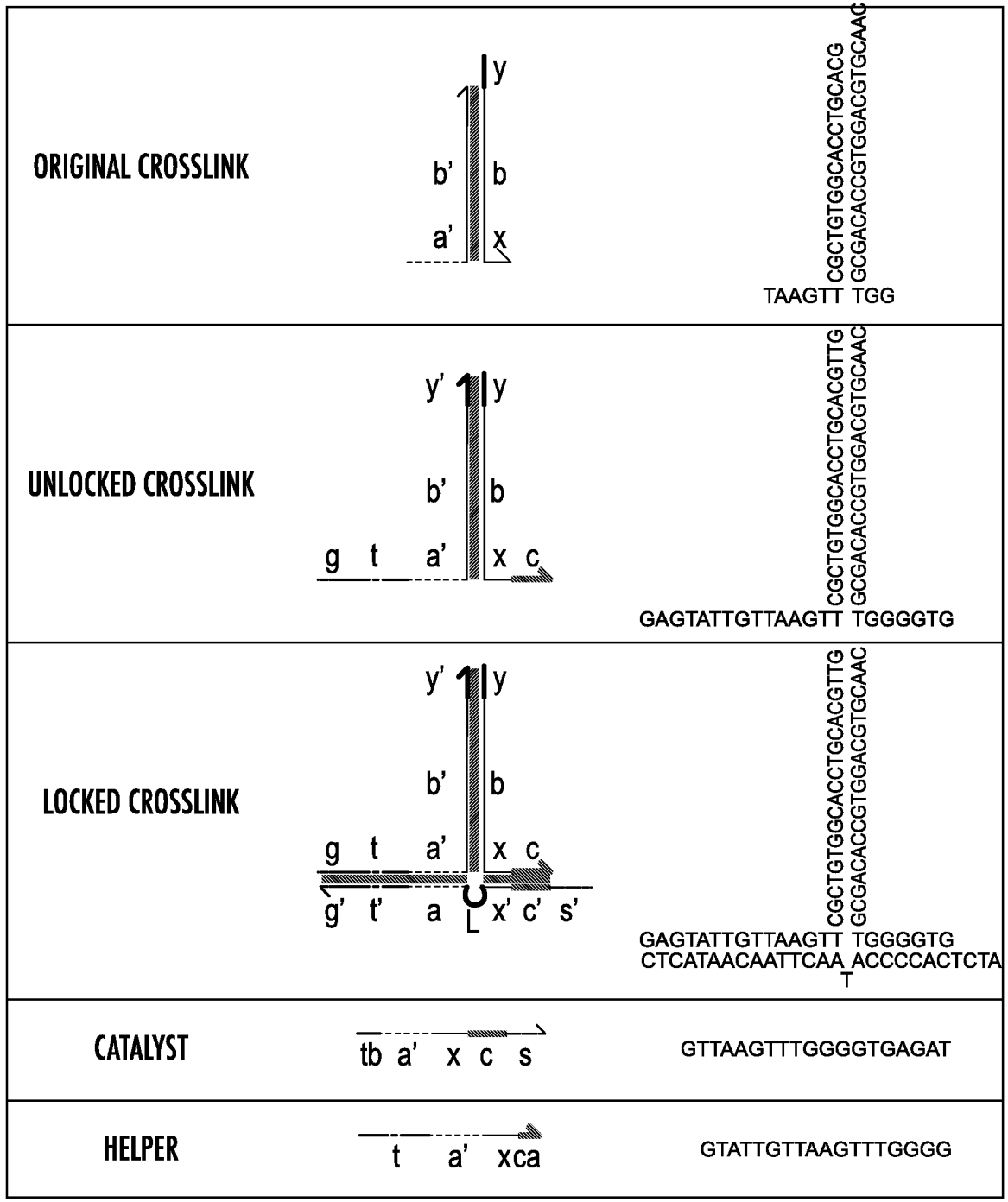
FIG. 24: DNA crosslink sequences. The original crosslink design is also used in Cangialosi et al. The additional sequences in the locked/unlocked crosslinks, Catalyst, and Helper strands were designed to have minimal nonspecific crosstalk with all other sequences using NUPACK. The hairpin fuel is inserted into the crosslink through initial interaction with the domains a' and x (teal and red domains). Figure discloses SEQ ID NOS 1, 2, 36, 37, 36, 37, 9, 12, and 11, respectively, in order of appearance.

Because the inputs to the controllers do not interact directly with the material, it is straightforward to create components where different stimuli can induce a response the expansion the same material. While it will be important to characterize interactions among the complex system of fuel, catalytic, and controller molecules we have created (e.g., FIG. 22), the modular design of the present system also suggests that there is no immediate barrier to increasing the complexity of the circuits that direct response. Controllers could now readily be built that employ further amplification, control expansion timing, or respond to single-base pair changes in inputs. The expansion demonstrated in this paper could direct material shape change. Building multiplexed circuits that each control the activity of crosslinks in a single material domain (FIG. 23) or different material domains could orchestrate complex shape change tasks.

Methods/Examples

The following Methods/Examples have been included to provide guidance to one of ordinary skill in the art for practicing representative embodiments of the presently disclosed subject matter. In light of the present disclosure and the general level of skill in the art, those of skill can appreciate that the following Methods/Examples are intended to be exemplary only and that numerous changes, modifications, and alterations can be employed without departing from the scope of the presently disclosed subject matter. The following Methods/Examples are offered by way of illustration and not by way of limitation.

Chemicals and DNA

Acrylamide (Bio-Rad, Cat. No. 161-0100) was solubilized using MilliQ purified water. Rhodamine B-conjugated acrydite monomer was obtained from PolySciences, Inc (Cat. No. 25404-100) and used for fluorescent visualization of hydrogels. Hydrogels were polymerized using the photoactive initiator Irgacure 2100 (BASF). ATP was purchased from Sigma (Cat. No. A6419) and solubilized to 53 mM using MilliQ purified water. Unmodified and acrydite-modified DNA strands were purchased with standard desalting purification from Integrated DNA Technologies, Inc. Fluorophore- and quencher-modified DNA was purchased with HPLC purification. All DNA was solubilized using TAE buffer (Life Technologies, Cat. No. 24710-030) supplemented with 12.5 mM magnesium acetate tetrahydrate (Sigma, Cat. No. M5661). As described in FIGS. 7, 16, 20, and 24, DNA sequences were designed using NUPACK or adapted from previous literature. Sequences used in this study are found in Table 1.

TABLE 1

List of sequences used in this study. Sequences were taken from either previous literature or designed using NUPACK as noted in FIGS. 7, 16, 20, and 24. The crosslinks A1HPCC(v1) and R1HPCC(v1) were used in FIG. 8 and for measuring the swelling of the hydrogels prepared without locks (data labeled "no locks" in figures. The experiment for FIG. 9 was conducted using A1 and R1 crosslinks. The crosslinks A1HPCC, R1HPCC, ASys2, and RSys2 were used for the particle swelling measurements presented in FIG. 23.

| Strand Name | Role | Sequence | SEQ ID NO: |
|---|---|---|---|
| Crosslinks | | | |
| A1 | Original Crosslink | /5Acryd/TAAGTT CGCTGTGGCACCTGCACG | 1 |
| R1 | Original Crosslink | /5Acryd/CAA CGTGCAGGTGCCACAGCG TGG | 2 |
| A1HPCC | Lockable Crosslink | 5/Acryd/TT GA GTATTGT TAAGTT CGCTGTGGCACCTGCACG TTG | 3 |
| R1HPCC | Lockable Crosslink | /5Acryd/CAA CGTGCAGGTGCCACAGCG TGG GGTG TTT | 4 |
| A1HPCC (v1) | Crosslink (S. FIG. 4, "no locks" data) | /5Acryd/TGGT TAAGTT CGCTGTGGCACCTGCACG TTG | 5 |
| R1HPCC (v1) | Crosslink (S. FIG. 4, "no locks" data) | /5Acryd/CAA CGTGCAGGTGCCACAGCG TGG GG | 6 |
| ASys2 | Sys. 2 Crosslink (S.FIG. 8) | /5Acryd/TT GT TATGTAT CTGTCT GCCTACCACTCCGTTGCG AAT | 7 |
| RSys2 | Sys. 2 Crosslink (S.FIG. 8) | /5Acryd/ATT CGCAACGGAGTGGTAGGC TTT GA AT TTT | 8 |
| Locking/Unlocking Strands | | | |
| Gb1HPCC | Locking Strand | ATCT CACC CCA T AACTTA ACAATAC TC | 9 |
| FC1HPCC | Key Strand | GA GTATTGT TAAGTT A TGG GGTG AGAT | 10 |
| Helper1HPCC | Helper Strand | GTATTGT TAAGTT TGG GG | 11 |
| Catalys1HPCC | Catalyst Strand | GT TAAGTT TGG GGTG AGAT | 12 |
| Hairpin Strands | | | |
| H1 | Hairpin Monomer | CCA CGCTGTGGCACCTGCACG CACCCA CGTGCAGGTGCCACAGCG AACTTA | 13 |
| H2 | Hairpin Monomer | TGGGTG CGTGCAGGTGCCACAGCG TAAGTT CGCTGTGGCACCTGCACG TTG | 14 |
| H1terminator | Hairpin Monomer | CCA CGCTGTGGCACCTGCACG TAGACT CGTGCAGGTGCCACAGCG AACTTA | 15 |
| H2terminator | Hairpin Monomer | TGGGTG CGTGCAGGTGCCACAGCG GCCTAG CGCTGTGGCACCTGCACG TTG | 16 |

TABLE 1-continued

List of sequences used in this study. Sequences were taken from either previous literature or designed using NUPACK as noted in FIGS. 7, 16, 20, and 24. The crosslinks A1HPCC(v1) and R1HPCC(v1) were used in FIG. 8 and for measuring the swelling of the hydrogels prepared without locks (data labeled "no locks" in figures. The experiment for FIG. 9 was conducted using A1 and R1 crosslinks. The crosslinks A1HPCC, R1HPCC, ASys2, and RSys2 were used for the particle swelling measurements presented in FIG. 23.

| Strand Name | Role | Sequence | SEQ ID NO: |
|---|---|---|---|
| *Logic Converter* | | | |
| Eo7Cat | Logic Gate | GTTAGATG AGAT GT AATTGATATG T GT GAG G AATGAT | 17 |
| GbEFG | Logic Gate | GTTCCCTGATCTTTA GCCTTA ATCATT C CTC AC A AC ATCT C CATCTAAC | 18 |
| G | Logic Gate | TAAGGC TAAAGATCAGGGAAC ACCATA | 19 |
| G.in | Logic Gate | TATGGT GTTCCCTGATCTTTA GCCTTA | 20 |
| Fcatst.in | Logic Input/Purification | GTTAGATG G AGAT GT T GT GAG G AATGAT TAAGGC | 21 |
| G.in.NoToe | Logic Gate Purification | GTTCCCTGATCTTTAGCCTTA | 22 |
| Wcatalyst_7 | Cat. Source (Logic) | GT TAAGTT TGG GGTG AGAT GT AATTGATATGT GT | 23 |
| GbC7 | Cat. Source (Logic) | AC CTC AC ACATATCAATT AC ATCT C | 24 |
| QW.F_7 | Cat. Source (Logic) Purification | G AGAT GT AATTGATATGT GT | 25 |
| *ATP Sensor/Converter* | | | |
| Cof.tapt_eta | Cofactor | TGAGG GT AGTGGAGTGAG G | 26 |
| Weta_ATPapt | ATP Sensor | GT AGTGGAGTGAG GT GAG G ACCTGGGGGAGTATTGCGGAGGAAGGT | 27 |
| Gbeta_ATPapt | ATP Sensor | CCAGGT C CTC AC CTCACTCCACT AC CCTCA | 28 |
| Wcatalyst_eta | Cat. Source (Sensor) | GT TAAGTT TGG GGTG AGAT GT AGTGGAGTGAG GT | 29 |
| GbCeta | Cat. Source (Sensor) | AC CTC AC CTCACTCCACT AC ATCT C | 30 |
| QW.F_eta | Cat. Source (Sensor) Purification | G AGAT GT AGTGGAGTGAG GT | 31 |
| *Controller Reporting Assay Strands* | | | |
| Rv(Wcat)q | Reporter | /5IABkFQ/GT TAAGTT TGG GG TG | 32 |
| Rb(Wcat)f | Reporter | C ATCT CA CC CCA AACTTA AC/36-FAM/ | 33 |
| PolyT20 | polyT | TTTTTTTTTTTTTTTTTTTT | 34 |

Preparation of DNA Complexes

DNA complexes were annealed in TAE buffer supplemented with 12.5 mM magnesium acetate (TAEM) from 90 to 20° C. using an Eppendorf PCR at 1° C./minute. Hydrogel crosslinker complexes were annealed at a stock concentration of 3 mM per strand while all other complexes were annealed at 100 µM. Hairpin-forming strands were flash cooled on ice for 3 minutes after heating to 95° C. for 10 minutes at a concentration of 80 µM. Hairpin and crosslinker complexes were not further purified. All other multi-strand circuit components (e.g., Source complexes) were PAGE purified after annealing using 15% polyacrylamide gels at 150 V for 3-4.5 hours. Immediately prior to PAGE purification, all complexes, with the exception of the ATP sensor complex, were incubated ~16-20 hours with 50 µM of their respective input strand with the toehold removed (see Table 1 for sequences). Fluorophore-/quencher-modified DNA complexes (Reporters) were not PAGE purified after annealing at 50 µM.

Synthesis of Poly(DNA-Co-Acrylamide) Hydrogel Particles

DNA crosslinks were mixed to a final concentration of 1.154 mM with water, 10×TAEM, acrylamide, rhodamine methacrylate, and Irgacure 2100 (75% v/v in butanol). The final concentrations of acrylamide, rhodamine methacrylate, and Irgacure 2100 were 1.41 M, 2.74 mM, and 3% (v/v), respectively. After mixing, the pre-polymer solutions were put under vacuum for 5 minutes. Pre-polymer droplets were prepared using a water-in-oil method (FIG. 2a). Mineral oil USP (CVS Pharmacy) "wells" were prepared on a cratered parafilm surface and pre-polymer droplets were added using a pipette set to 0.25 µL. Droplets were exposed to 365 nm light using a Benchtop 3UV Transilluminator (UVP) for 1 minute (~4 mW/cm$^2$) to polymerize and crosslink the particles. Particles were purified from the oil using centrifugation into TAEM and were stored at 4° C. until use, usually within 1 week.

Swelling of DNA-Crosslinked Hydrogels

Swelling experiments were conducted in 96-well plates (Fisher Scientific) with one particle per well. Micrographs of particles were taken on an IX73 Olympus fluorescence microscope using a rhodamine filter. The final volume of liquid in each well varied between 100-120 µL, depending on the experiment. For experiments with locked particles, the particles were incubated with DNA hairpins (20 µM/hairpin type, 10% terminator) for about 24 hours prior to the addition of Catalyst/Helper strands or circuit complexes. For all experiments with DNA circuits, the Helper strand concentration was 10 µM. Images of each particle were captured every 30 minutes.

Particle Area Measurement and Analysis

Images of the fluorescent particles were considered to be accurate 2D projections of the particle size near the center xy-plane. To decrease the sensitivity and bias involved in measuring the diameter, especially of an irregular or non-circular projection, the area of the 2D projection was chosen as the representative variable of particle size and calculated as a function of time for each particle. The area was determined using standard intensity-based thresholding and mask image analysis using MATLAB (Described below in "Measuring the area of a particle's 2D fluorescence projection"). Area measurements for each particle were normalized to the initial time point. The curves showing the change in size as a function of time are taken from measurements made every 30 minutes, averaged over multiple particles. The curves were smoothed with a window size of 3.

Measuring the Area of a Particle's 2D Fluorescence Projection

The area of the 2D projection of each particle in the fluorescence micrographs (FIG. 5) was calculated using custom built MATLAB scripts developed using standard edge-detection algorithms. The algorithm used thresholding to determine the boundaries of the particles. This threshold value was calculated using the following method:

1. Normalize the image to the highest and lowest intensity.

$$normImage = \frac{Image - \min(Image)}{\max(Image) - \min(Image)} \quad (1)$$

2. Use MATLAB's built-in global threshold calculator graythresh.

$$globalThresh = graythresh(normImage) \quad (2)$$

3. Adjust the global threshold for the non-normalized image and image-specific adjustments.

$$initialThresh = globalThresh*(\max(Image)-\min(Image))+\min(Image) \quad (4)$$

$$intThreshOrig = initialThresh \text{ of 1st image in time series} \quad (5)$$

$$\beta = \frac{mean(Image)*\alpha}{intThreshOrig} \quad (6)$$

$$1.1 \leq \alpha \leq 3 \quad (7)$$

$$particlePixels = Image > \beta*initialThresh \quad (8)$$

where α corresponds to a manual input that was adjusted until a close match between the visible particle boundaries and the calculated boundaries was found. For particles that did not have significant intensity changes over the course of the experiment (i.e., particles that did not swell to a significant extent), α did not need to be adjusted between images in a time series. For some particles that did swell, and thus did have significant intensity changes, α was manually adjusted about every 5 images. After determining the pixels corresponding to the particle, the particle's area and boundary were extracted using the functions regionprops and bwboundaries. Examples of processed images are shown in FIG. 5.

Fluorophore-Quencher Assay of DNA Strand-Displacement Controller Circuits

An Agilent Stratagene Mx3000 or Mx3005 was used to test the operation of the DNA-based circuits in the absence of hydrogel particles. A reporter complex, using FAM and IowaBlackFQ fluorophore-/quencher-modified DNA, was designed to increase measured fluorescence upon reaction with DNA strands containing the Catalyst sequence and toehold (FIG. 17). The measured fluorescence increase was converted into the concentration of Catalyst strand using a calibration curve. The DNA strand-displacement logic circuit was run with 200 nM Source complexes and 200 nM Reporter. Aptasensor circuits were run at 100 nM Source complexes, 100 nM Cofactor strand, and 200 nM Reporter. PolyT$_{20}$ (1 μM) was added at to inhibit adsorption to well walls.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of unlocking a locked gel comprising the steps of:
   providing a locked gel comprising a polymer comprising a nucleic acid cross link and a nucleic acid lock in a locked conformation preventing the locked gel from reacting with other nucleic acid sequences;
   adding a nucleic acid key that binds to the nucleic acid lock of the locked gel and further comprising a helper that binds to the nucleic acid lock that is bound to the nucleic acid key that allows the nucleic acid key to react with further nucleic acid sequences; and
   changing the nucleic acid lock into an unlocked conformation, wherein the gel can react with other nucleic acid sequences.

2. The method of claim 1, wherein there is 1 or more molar parts of nucleic acid key and the nucleic acid lock is in the range of 6 to 120 molar parts in the locked gel.

3. The method of claim 1, wherein the nucleic acid key is in a concentration range of 1 nM to 500 nM.

4. The method of claim 1, wherein the nucleic acid key is in a concentration range of 10 nM to 400 nM.

5. The method of claim 1, wherein a total concentration of helper is in the range of 1-20 molar parts of helper to 1 molar part of the nucleic acid lock in the locked gel.

6. The method of claim 1, wherein the helper is in a concentration range of 1 uM to 20 uM.

* * * * *